(12) United States Patent
Lange et al.

(10) Patent No.: US 8,138,174 B2
(45) Date of Patent: Mar. 20, 2012

(54) COMPOUNDS WITH A COMBINATION OF CANNABINOID $CB_1$ ANTAGONISM AND SEROTONIN REUPTAKE INHIBITION

(75) Inventors: Josephus H. M. Lange, Weesp (NL); Cornelis G. Kruse, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 380 days.

(21) Appl. No.: 11/970,229

(22) Filed: Jan. 7, 2008

(65) Prior Publication Data
US 2008/0214559 A1 Sep. 4, 2008

Related U.S. Application Data

(60) Provisional application No. 60/879,533, filed on Jan. 10, 2007.

(51) Int. Cl.
*A61K 31/55* (2006.01)
(52) U.S. Cl. .............. 514/217.09; 514/254.05; 540/603; 544/370
(58) Field of Classification Search .................. 540/603; 544/370
See application file for complete search history.

(56) References Cited

U.S. PATENT DOCUMENTS

2005/0054679 A1\* 3/2005 Kruse et al. .................. 514/326

FOREIGN PATENT DOCUMENTS

| WO | WO 03/007887 A2 | 1/2003 |
| WO | WO 03/063781 A2 | 8/2003 |
| WO | WO 2004/013120 A1 | 2/2004 |
| WO | WO 2006/061372 A2 | 6/2006 |
| WO | WO 2006/061374 A1 | 6/2006 |
| WO | WO 2006/061376 A1 | 6/2006 |

OTHER PUBLICATIONS

West, Anthony R., Solid State Chemistry and its Applications, Wiley, New York, 1988, pp. 358 and 365.\*
Wolff, Manfred E. "Burger's Medicinal Chemistry, 5ed, Part I", John Wiley & Sons, 1995, pp. 975-977.\*
Banker (Modern Pharmaceutics) Banker, G.S. et al, "Modern Pharmaceutics, 3ed.", Marcel Dekker, New York, 1996, pp. 451 and 596.\*
Borisy et al. Systematic discovery of multicomponent therapeutics. 2003, Proceedings of the National Academy of Sciences of the United States of America. 100, 7977-7982.\*
International Search Report and Written Opinion, Dated Mar. 13, 2008, issued in PCT/EP2008/050181.
Communication from the European Patent Office regarding Application No. 08 701 345.4-2101, dated May 31, 2010.
International Preliminary Report on Patentability regarding International Application No. PCT/EP2008/050181, dated Mar. 25, 2009.

\* cited by examiner

*Primary Examiner* — James O Wilson
*Assistant Examiner* — Brian McDowell
(74) *Attorney, Agent, or Firm* — Finnegan, Henderson, Farabow, Garrett & Dunner LLP

(57) ABSTRACT

Compounds with a combination of cannabinoid $CB_1$ antagonism and serotonin reuptake inhibition, pharmaceutical compositions containing these compounds, methods for preparing these compounds, methods for preparing novel intermediates useful for their synthesis, and methods for preparing these compositions are disclosed. Uses of such compounds and compositions, particularly their use in administering them to patients to achieve a therapeutic effect in psychosis, anxiety, depression, attention deficits, cognitive disorders, obesity, drug dependence, Parkinson's disease, Alzheimer's disease, pain disorders, neuropathic pain disorders and sexual disorders are disclosed.
In at least one embodiment, the invention relates to compounds of the general formula (1):

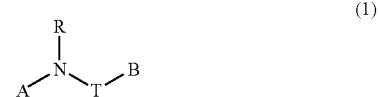

(1)

wherein the substitutents have the definitions given in the specification.

5 Claims, No Drawings

COMPOUNDS WITH A COMBINATION OF CANNABINOID $CB_1$ ANTAGONISM AND SEROTONIN REUPTAKE INHIBITION

This application claims the benefit of priority of U.S. Provisional Application No. 60/879,533, filed on Jan. 10, 2007, the disclosure of which is incorporated herein by reference.

This invention relates to the fields of pharmaceutical and organic chemistry, and provides compounds with a combination of cannabinoid $CB_1$ antagonism and serotonin re-uptake inhibition, intermediates, formulations, methods for preparing these compounds, methods for preparing compositions comprising these compounds, and methods of treatment using these compounds.

A reductionist 'one target—one disease' approach has dominated the pharmaceutical industry for some decades. Using this strategy, many successful drugs were discovered. Despite these successes, many diseases remain inadequately treated. These findings rationalize an alternative approach, wherein chemical entities are developed that simultaneously modulate multiple targets. Such drugs may show advantageous properties such as increased clinical efficacy, lack of undesired pharmacokinetic drug-drug interactions, or lack of unfavorable pharmacokinetic and pharmacodynamic properties. Unfavorable pharmacokinetic and pharmacodynamic properties may lead to unpredictable variability between individual patients. In order to combine different therapeutic mechanisms, cocktails of two or more drugs are still used in clinical practice. Alternatively, multicomponent drugs are being used wherein two or more pharmaceutically active compounds are co-formulated in a single tablet or capsule in order to improve patient compliance. Another approach utilizes a pharmaceutical treatment with a chemical entity that is able to modulate more than one biological target simultaneously. It is clear that such a 'single entity—multiple target approach' offers the advantage of a lower risk of undesired drug-drug interactions compared to drug cocktails or multicomponent drugs. Several multiple target ligands are known. The majority were found retrospectively or by accident; only a few were rationally designed.

Cannabinoid receptors are part of the endo-cannabinoid system, involved in many diseases. Detailed information on cannabinoid receptors, $CB_1$ receptor modulators, and their pharmacological activities are the subject of recent reviews (Landsman, 1997; Lichtman, 2002; De Petrocellis, 2004; Di Marzo, 2004; Hertzog, 2004; Lange, 2004, 2005; Smith, 2005; Thakur, 2005; Padgett, 2005; Muccioli, 2005; Lambert, 2005; Vandevoorde, 2005). Potential therapeutic applications of $CB_1$ receptor modulators disclosed in the quoted reviews include medicaments for treating psychosis, anxiety, depression, attention deficits, memory disorders, cognitive disorders, appetite disorders, obesity, addiction, appetence, drug dependence, neurodegenerative disorders, dementia, dystonia, muscle spasticity, tremor, epilepsy, multiple sclerosis, traumatic brain injury, stroke, Parkinson's disease, Alzheimer's disease, epilepsy, Huntington's disease, Tourette's syndrome, cerebral ischaemia, cerebral apoplexy, craniocerebral trauma, spinal cord injury, neuroinflammatory disorders, plaque sclerosis, viral encephalitis, demyelinisation related disorders, pain disorders, including neuropathic pain disorders, septic shock, glaucoma, diabetes, cancer, emesis, nausea, gastrointestinal disorders, gastric ulcers, diarrhea, sexual disorders, impulse control disorders, and cardiovascular disorders.

Mood disorders and anxiety disorders cause enormous suffering. The introduction of selective serotonin reuptake inhibitors more than two decades ago has been a major step in the evolution of safer antidepressants. Representative examples of selective serotonin reuptake inhibitors are fluvoxamine, fluoxetine, paroxetine, sertraline, citalopram, zimeldine, clomipramine, indalpine, and indatraline. In spite of the remarkable structural diversity, most selective serotonin reuptake inhibitors are mono-amine-based: they contain a basic nitrogen atom (Pacher, 2004). Scientific articles, patents and patent applications indicate the following therapeutic applications for serotonin reuptake inhibitors: alcoholism, Alzheimer's disease, anorexia nervosa, anxiety disorder, attention deficit hyperactivity disorder, bipolar disorder, bulimia nervosa, bentral nervous system disease, chemotherapy induced emesis, cocaine addiction, cognitive disorder, diabetic neuropathy, drug dependence, eating disorder, female sexual dysfunction, functional bowel disorder, generalized anxiety disorder, headache, inflammation, irritable bowel syndrome, male sexual dysfunction, major depressive disorder, menopause, migraine, myalgia, neuralgia, neuropathic pain, obesity, obsessive compulsive disorder, osteoarthritis, pain, panic disorder, Parkinson's disease, premature ejaculation, premenstrual syndrome, psychosexual disorder, psychosis, rheumatoid arthritis, schizophrenia, sleep disorder, and urinary incontinence.

Because of the frequently observed co-morbidity of symptoms of different diseases, compounds combining cannabinoid $CB_1$ antagonism with serotonin reuptake inhibition can be useful to treat the conditions wherein either a cannabinoid $CB_1$ antagonist or a serotonin reuptake inhibitor is potentially effective. Thus the compounds of the invention can be used for treating: addiction, alcoholism, Alzheimer's disease, anorexia nervosa, anxiety disorder, appetite disorders, attention deficit hyperactivity disorder, bipolar disorder, bulimia nervosa, cancer, cardiovascular disorders, central nervous system disease, cerebral ischaemia, cerebral apoplexy, chemotherapy induced emesis, cocaine addiction, cognitive disorder, dementia, demyelinisation related disorders, diabetes, diabetic neuropathy, diarrhea, drug dependence, dystonia, eating disorder, emesis, epilepsy, female sexual dysfunction, functional bowel disorder, gastrointestinal disorders, gastric ulcers, generalized anxiety disorder, glaucoma, headache, Huntington's disease, impulse control disorders inflammation, irritable bowel syndrome, male sexual dysfunction, major depressive disorder, memory disorders menopause, migraine, muscle spasticity, multiple sclerosis, myalgia, nausea, neuralgia, neurodegenerative disorders, neuroinflammatory disorders, neuropathic pain, obesity, obsessive compulsive disorder, osteoarthritis, pain, panic disorder, Parkinson's disease, plaque sclerosis, premature ejaculation, premenstrual syndrome, psychosexual disorder, psychosis, rheumatoid arthritis, septic shock, schizophrenia, sexual disorders, sleep disorder, spinal cord injury, stroke, Tourette's syndrome, traumatic brain injury, tremor, urinary incontinence, and viral encephalitis.

Of particular importance is the use of the compounds of the invention for treating disorders claimed to be treatable with cannabinoid $CB_1$ antagonists as well as with serotonin reuptake inhibitors. Attacking such disorders simultaneously via two different mechanisms of action can have synergistic effects. Thus, the compounds of the invention may be particularly useful for treating: psychosis, anxiety, depression, attention deficits, cognitive disorders, obesity, drug dependence, Parkinson's disease, Alzheimer's disease, pain disorders, neuropathic pain disorders, and sexual disorders.

The pharmacophore of the majority of cannabinoid $CB_1$ receptor antagonists was the subject of several reviews (Lange, 2005; Reggio, 2003). Scheme 1 generally depicts the pharmacophore of the majority of cannabinoid $CB_1$ receptor antagonists.

Scheme 1: $CB_1$ receptor antagonist pharmacophore, and one of its putative key interactions with the $CB_1$ receptor Asp366-Lys192

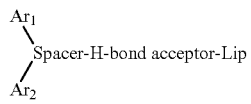

In Scheme 1, Ar1 and Ar2 are phenyl groups, optionally substituted with one or two halogen atoms, trifluoromethyl groups, or methoxy groups. In Scheme 1, the 'spacer' contains a five-membered heterocyclic group such as 4,5-dihydropyrazole, imidazole, pyrazole, thiazole, thiophene or pyrrole, or the spacer contains a phenyl group or a six-membered heterocyclic group such as pyridine, pyrimidines or pyrazine. The spacer can also contain an azetidine moiety, a 1,3-benzodioxole moiety or an alkyl moiety like in MK-0364 (see below). In addition, one of the groups Ar1 or Ar2 can be fused to the spacer, or can be connected to the spacer by an additional ring: so-called conformational constraint. Several kinds of conformational constraints have successfully been implemented in this pharmacophore model. The H-bond acceptor represents a carbonyl group, a sulfonyl group or a nitrogen-atom which may be free or embedded in a heterocyclic ring structure such as an imidazole ring. In Scheme 1, 'Lip' represents a lipophilic moiety, for instance piperidin-1-ylamino, pyrrolidinyl-1-amino, cycloalkylamino, phenylamino, arylamino, benzylamino, or alkylamino.

Molecular modeling studies indicate that the presence of a hydrogen bond acceptor is crucial: that is thought to interact with the Lys-192 amino acid residue side chain in the $CB_1$ receptor, thereby stabilizing its inactive state.

To illustrate the $CB_1$ receptor antagonist pharmacophore model, a number of concrete examples of $CB_1$ receptor antagonists are depicted below. The putative hydrogen bond acceptor atom (oxygen atom from a carbonyl group, oxygen atom from a sulfonyl group, or nitrogen atom in a heteroaromatic ring) is indicated bold.

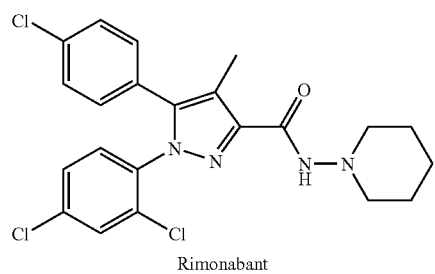

Rimonabant

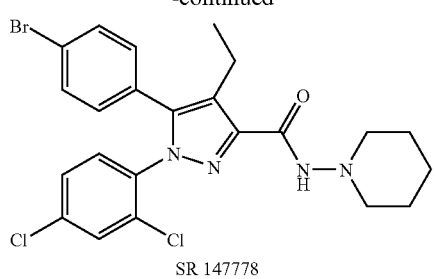

SR 147778

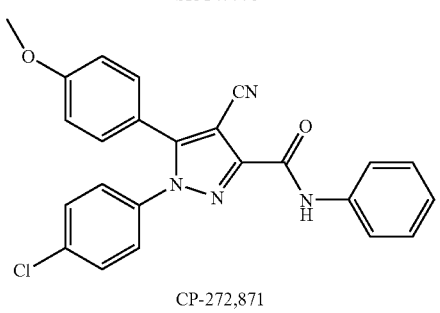

CP-272,871

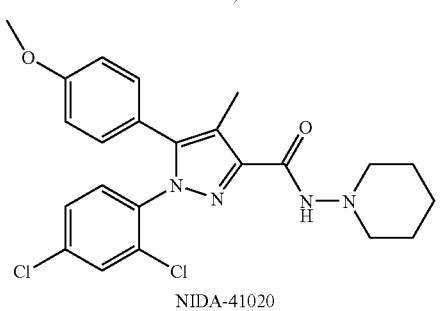

NIDA-41020

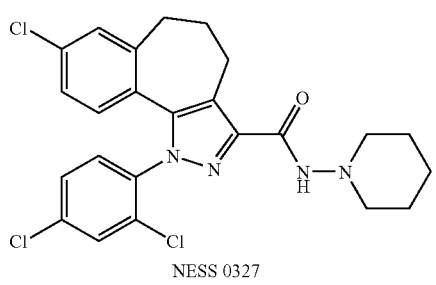

NESS 0327

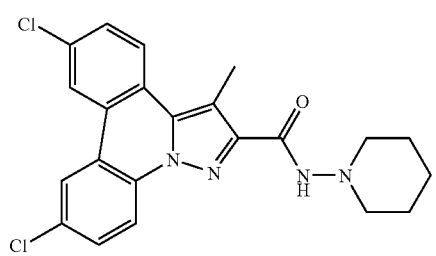

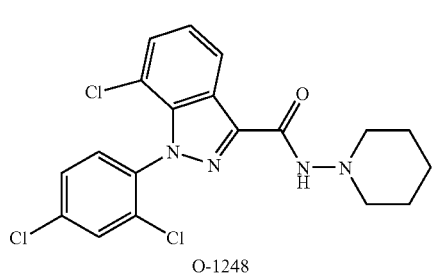

O-1248

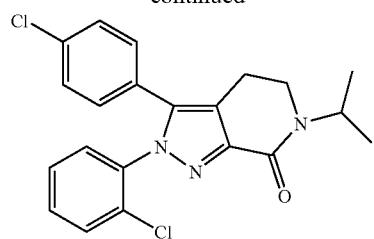
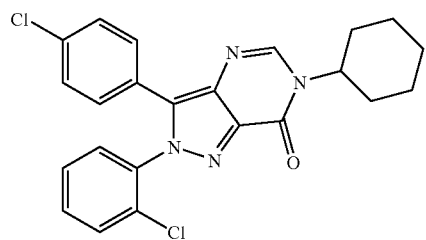
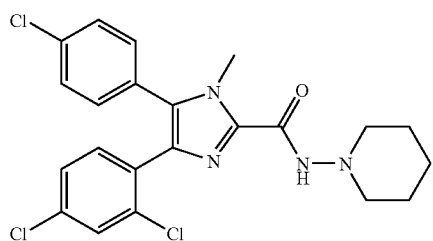
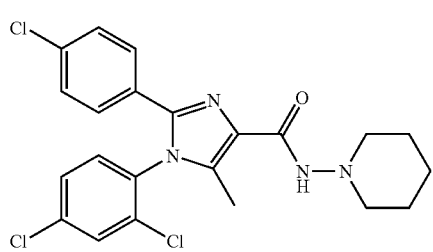
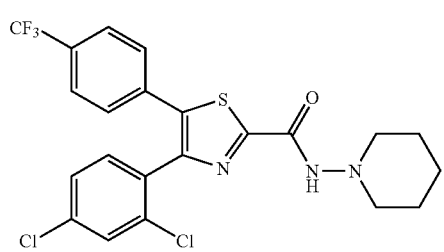
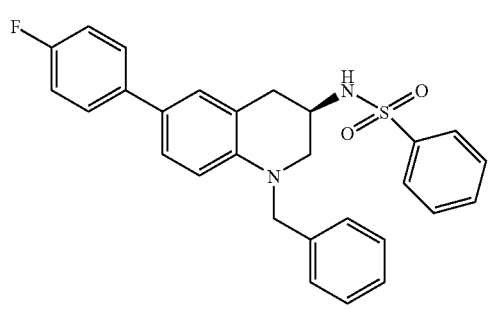
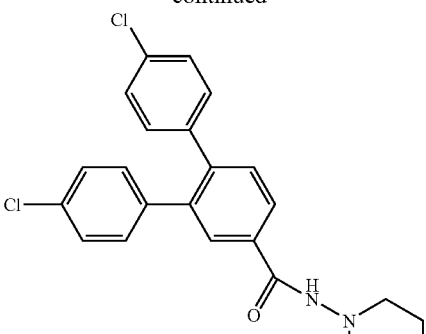
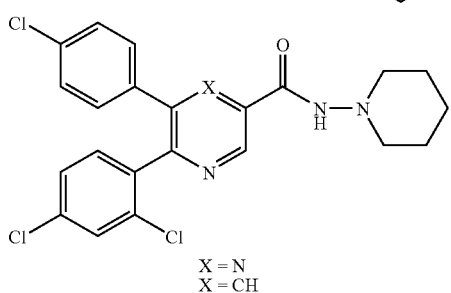
X = N
X = CH
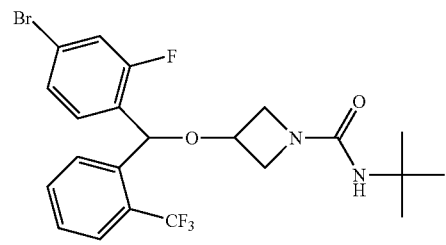
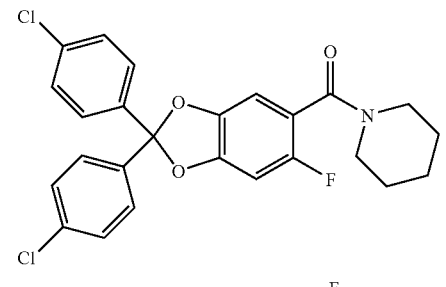
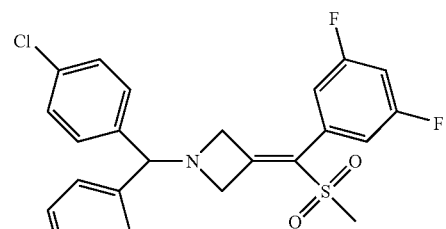
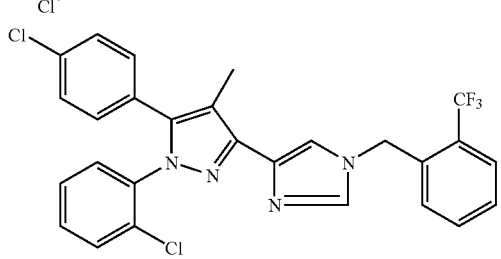

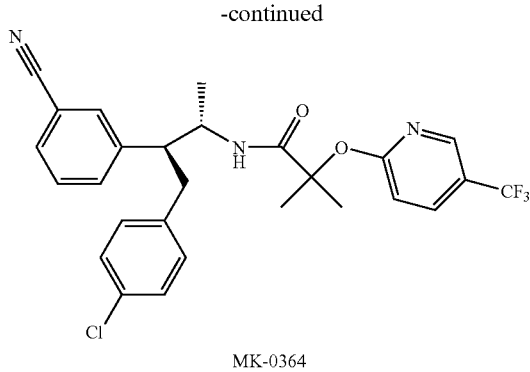

MK-0364

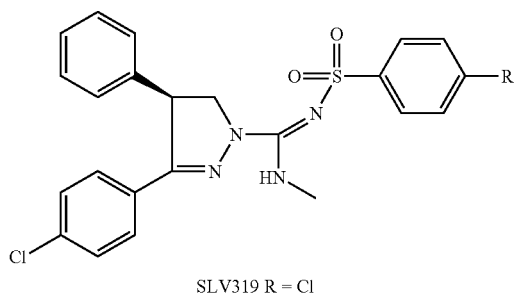

SLV319 R = Cl
SLV326 R = CF₃

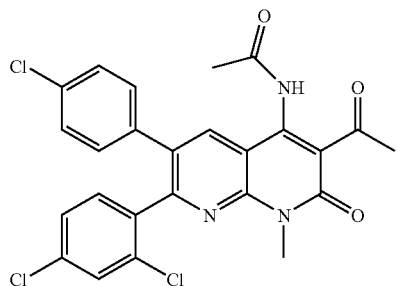

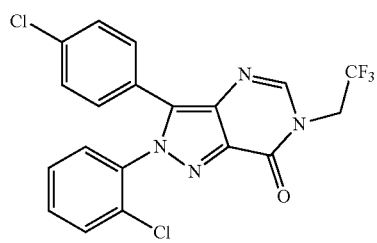

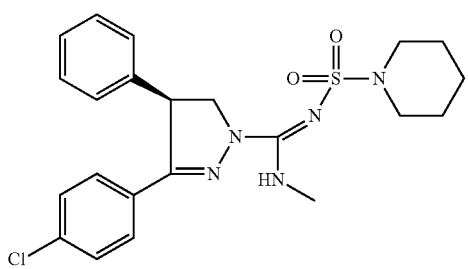

A pharmacophore model of serotonin reuptake inhibitors has been reported (Bureau, 2002). Scheme 2 generally depicts the pharmacophore of serotonin reuptake inhibitors:

Scheme 2: Schematic overview of the SRI pharmacophone

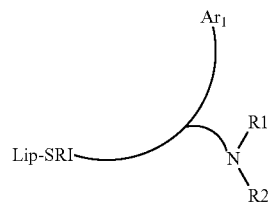

It is characterized by a basic nitrogen atom (N), a lipophilic extended aromatic region (Ar1) and a lipophilic part (Lip-SRI). The basic amino function may be unsubstituted (i.e. R1 and R2 represent hydrogen) like in fluvoxamine, or mono substituted like in fluoxetine, indatraline, and sertraline, or disubstituted like in citalopram, zimeldine, and clomipramine. The basic nitrogen atom may be part of a six-membered ring such as in indalpine and paroxetine (i.e. R1 represents a hydrogen atom and R2 is part of the pharmacophore carbocyclic framework). Many 4-(3-indolyl-alkyl)piperidine derivatives, including indalpine and 4-(3-indolyl-alkyl)piperazine derivatives have been shown to possess potent serotonin reuptake inhibitor activity (Le Fur, 1977; Malleron, 1993).

The selective $CB_1$ receptor antagonist SR141716A (rimonabant) has been known for more than a decade. Many other selective $CB_1$ antagonists were invented later. Serotonin reuptake inhibitors have been known for more than two decades. Thus far, no compounds have been disclosed that combine $CB_1$ receptor antagonism with serotonin reuptake inhibitor activity.

An objective of the present invention was to develop compounds with a combination of $CB_1$ antagonism and serotonin reuptake inhibition.

Disclosure

It was found that molecules containing structural (activity related) components of known cannabinoid $CB_1$ antagonists and structural (activity related) components of the known serotonin reuptake inhibitors indalpine and fluvoxamine, share the activity of both molecules from which they were derived: cannabinoid $CB_1$ antagonism and serotonin reuptake inhibition. This invention relates to compounds with a combination of cannabinoid $CB_1$ antagonism and serotonin reuptake inhibition, for example, compounds having a $pK_i$-value>6.00 in both $CB_1$ receptor binding and serotonin reuptake binding.

In at least one embodiment, the invention relates to compounds of formula (1):

(1)

or tautomers, stereoisomers, N-oxides, and isotopically-labelled analogues thereof, and to pharmacologically acceptable salts, hydrates and solvates of any of the foregoing, wherein:

A is a structural (activity related) component of any known cannabinoid $CB_1$ antagonist comprising at least two phenyl rings, each phenyl ring is optionally substituted with one or two substituents chosen from halogen atoms, a methoxy group, and a trifluoromethyl group, said structural element A being attached to a hydrogen bond acceptor in said cannabinoid CB₁ antagonist, wherein the hydrogen bond acceptor moiety is chosen from a carbonyl group, a sulfonyl group, a nitrogen atom, and an oxygen atom incorporated in a heteroaromatic ring structure, N is a non-basic nitrogen atom, T is a saturated or unsaturated carbon chain having from 0-8 carbon atoms, wherein one carbon atom in the chain may be replaced with a nitrogen atom, optionally substituted with a ($C_1$-$C_3$)-alkyl or $CH_2CF_3$ group, or replaced with an oxygen atom or a sulphur atom, and wherein the chain is optionally substituted with one or more substituents chosen from fluoro, amino, cyano, ($C_1$-$C_3$)alkyl, ($C_1$-$C_3$)alkoxy, and trifluoromethyl, R is chosen from a hydrogen atom, and a ($C_1$-$C_3$)-alkyl group, or R together with the nitrogen atom to which it is attached, and together with a part of T, forms a ($C_4$-$C_7$)-heterocycloalkyl or a heteroaryl group, and B is a structural (activity related) component of any known serotonin reuptake inhibitor.

Other embodiments provide one or more compounds of formula (1) wherein A is a structural (activity related) component of a cannabinoid CB₁ antagonist chosen from:

11C-JHU-75528, A-796260, ajulemic acid, AM 251, AM 630, AVE-1625, CP-272871, CP-945598, EMD-68843, GRC-10389, LY-2077855, LY-320135, NIDA-41020, O-2093, SLV319, SLV326, SR-140098, SR-144385, SR-41716A (rimonabant), surinabant, V-24343, WIN-54461, and WIN-56098, and B is a structural (activity related) component of a 5-HT reuptake inhibitor chosen from:

403U76, A-80426, AD-337, adinazolam, agomelatine, alaproclate, amineptine, amitriptyline, ARAK-0029, ARAK-0051, befetupitant, befloxatone, BGC-20-1259, bicifadine, BMS-505130, brofaromine, bupropion, butriptyline, cericlamine, citalopram, CL:-275838, clomipramine, clovoxamine, CX-157, dapoxetine, desvenlafaxine, dexfenfluramine, dibenzepin, diclofensine, dosulepine, DOV-21947, DOV-102677, DOV-216303, duloxetine, DU 125530, DuP-631, EN-3215, EpiCept NP-1, escitalopram, femoxetine, fluoxetine, (S)-fluoxetine, fluvoxamine, gepirone, IDN-5491, imipramine, indalpine, iprindole, L-792239, LI-301, litoxetine, lofepramine, LU-10134-C, LU-AA21004, lubazodone, LY-214281, LY-367265, LY-393558, maprotiline, MCl-225, MCL-0042, McN-5652, melitracen, mianserine, milnacipran, mirtazepine, moclobemide, modafinil, nefazodone, 6-nitroquipazine, nortriptyline, NR-200s, NS-2381, NS-2389, NS-2463, NS-4194, NS-23459, omiloxetine, OPC-14523, opipramol, Org-6582, paroxetine, pramipexole, PRC-025, propizepine, quetiapine, quinupramine, ramelteon, R-fluoxetine, rizatriptan, robalzotan, roxindole, RS-1439, SB-649915, S-9977, SD-726, selegiline, SEP-225289, SEP-227162, sertraline, sibutramine, (S)-sibutramine, (R)-didemethylsibutramine, SLV310, SLV314, SPD-473, tramadol, trazodone, udenafil, UK-416244, UP-23761, VANH-36, venlafaxine, vilazodone, VML-670, VN-2222, volinanserin, WF-23, Wf-516, WL-1011, WL-1017, YM-922, and zimeldine.

Further embodiments provide one or more compounds of formula (1), wherein A is chosen from one of the fragments ($A^{1a}$), ($A^{1b}$), ($A^2$), ($A^3$) ($A^4$), ($A^5$), ($A^6$), ($A^7$), and ($A^8$):

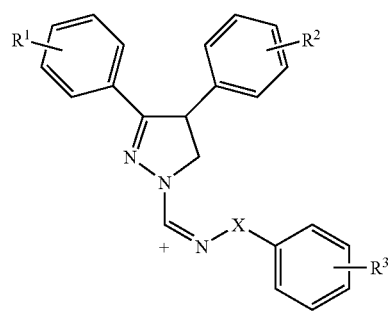

($A^{1a}$)

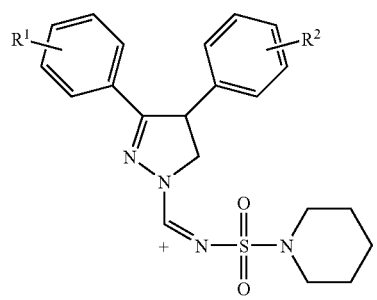

($A^{1b}$)

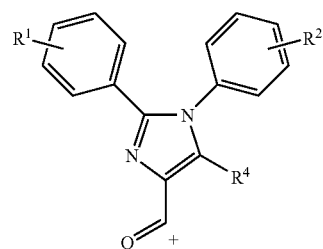

($A^2$)

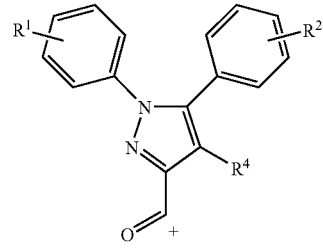

($A^3$)

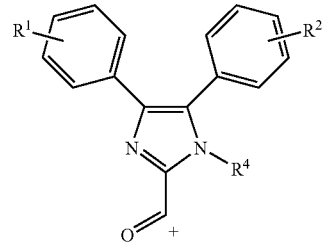

($A^4$)

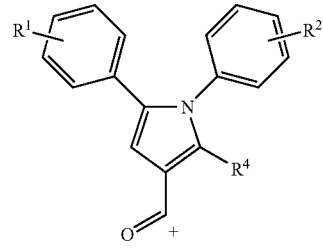

($A^5$)

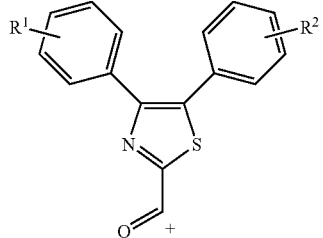
(A⁶)

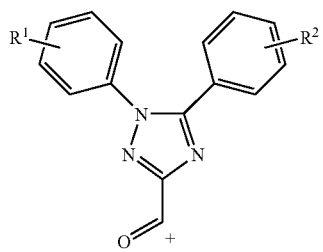
(A⁷)

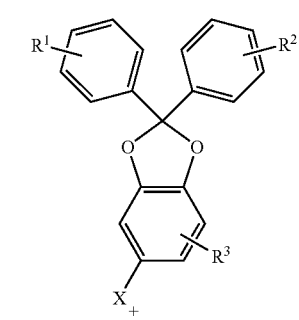
(A⁸)

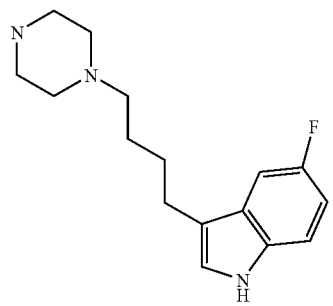
(NRTB¹)

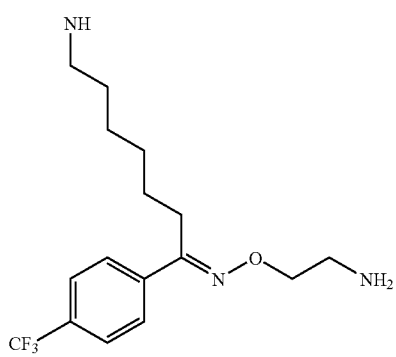
(NRTB²)

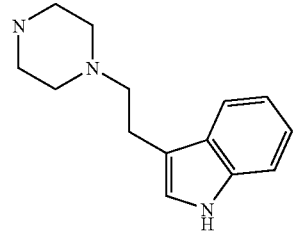
(NRTB³)

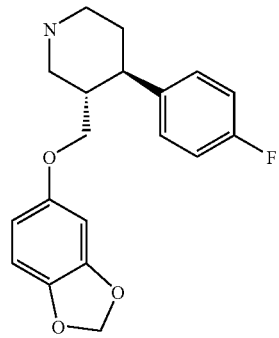
(NRTB⁴)

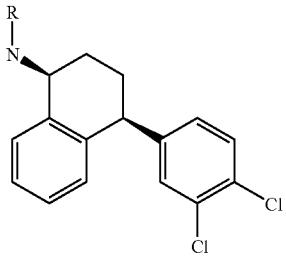
(NRTB⁵)

wherein, X is chosen from a sulfonyl and a carbonyl group, the "+" symbol is the position at which the fragment is attached to moiety N (wherein N is a non-basic nitrogen atom) in formula (1), $R^1$, $R^2$ and $R^3$ independently are chosen from a hydrogen atom, a trifluoromethyl group and halogen atoms, $R^4$ is chosen from a hydrogen atom, halogen atoms, methyl, ethyl, trifluoromethyl, hydroxymethyl, fluoromethyl, 2,2,2-trifluoroethyl, propyl, methylsulfanyl, methylsulfinyl, methylsulfonyl, ethylsulfanyl, ethylsulfinyl, ethylsulfonyl, $C_{1-3}$-dialkyl-aminomethyl, pyrrolidin-1-ylmethyl, piperidin-1-ylmethyl, and morpholin-4-ylmethyl groups, and the other substituents have the definitions as given above.

In another embodiment, the invention relates to compounds of formula (1), wherein A is chosen from one of the fragments ($A^{1a}$), ($A^{1b}$), ($A^2$), ($A^3$) ($A^4$), ($A^5$), ($A^6$), ($A^7$), and ($A^8$), and the NRTB sequence of formula (1) is chosen from one of the fragments (NTRB¹), (NRTB²), (NRTB³), (NRTB⁴), (NRTB⁵), (NRTB⁶), (NRTB⁷), (NRTB⁸), (NRTB⁹) and (NRTB¹⁰:

-continued (NRTB⁶)
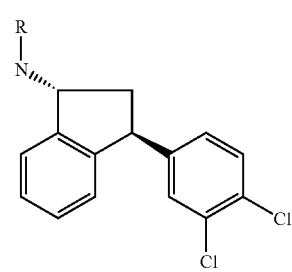

(NRTB⁷)
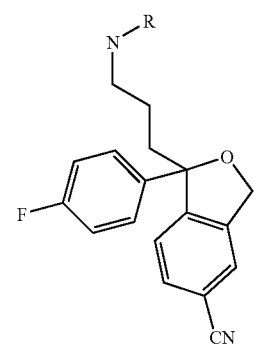

(NRTB⁸)
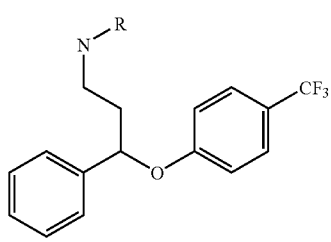

(NRTB⁹)
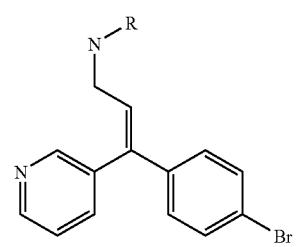

(NRTB¹⁰)
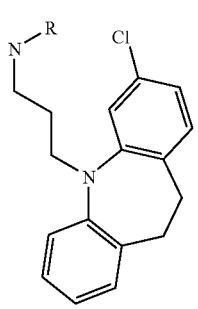

wherein R is chosen from a hydrogen atom and a (C₁-C₃)-alkyl group.

In another embodiment, the invention relates to compounds of formula (1), wherein A is chosen from one of the fragments (A¹ᵃ) and (A²):

(A¹ᵃ)
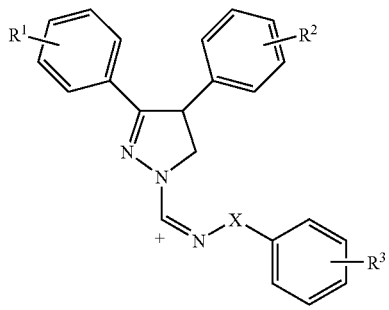

(A²)
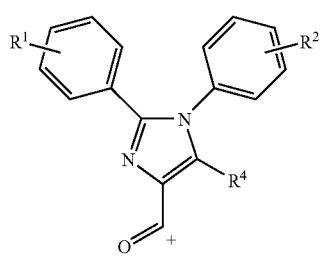

wherein, X is chosen from a sulphonyl and a carbonyl group, the "+" symbol is the point at which the fragment is attached to the non-basic nitrogen atom N in formula (1), R¹, R² and R³ independently are chosen from hydrogen, trifluoromethyl and halogen, R⁴ is chosen from a hydrogen atom, halogen atoms, methyl, ethyl, trifluoromethyl, hydroxymethyl, fluoromethyl, 2,2,2-trifluoroethyl, propyl, methylsulfanyl, methylsulfinyl, methylsulfonyl, ethylsulfanyl, ethylsulfinyl, ethylsulfonyl, C₁₋₃-dialkyl-aminomethyl, pyrrolidin-1-ylmethyl, piperidin-1-ylmethyl, and morpholin-4-ylmethyl group, and the other substituents have the definitions as given above.

In another embodiment, the invention relates to compounds of formula (1), wherein A is chosen from one of the fragments (A¹ᵃ) and (A²), and the NRTB sequence of formula (1) is chosen from one of the fragments (NTRB¹), (NRTB²), (NTRB³), (NRTB⁴), (NRTB⁵), (NRTB⁶), (NRTB⁷), (NRTB⁸), (NTRB⁹) and (NRTB¹⁰).

In another embodiment, the invention relates to compounds of formula (1), wherein A is chosen from one of the fragments (A³) and (A⁴):

(A³)
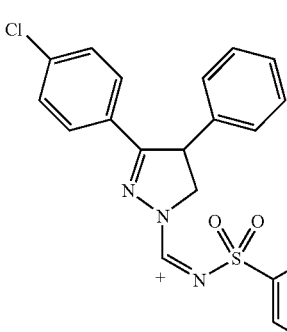

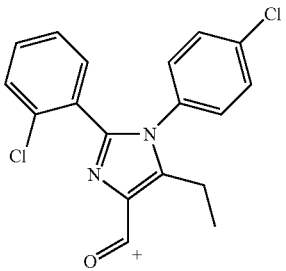
and the NRTB sequence of formula (1) is chosen from one of the fragments (NTRB[1]), (NRTB[2]), (NTRB[3]), (NRTB[4]), (NRTB[5]), (NTRB[6]), (NTRB[7]), (NRTB[8]), (NRTB[9]) and (NRTB[10]).
In another embodiment, the invention relates to compounds of formula (1) chosen from:
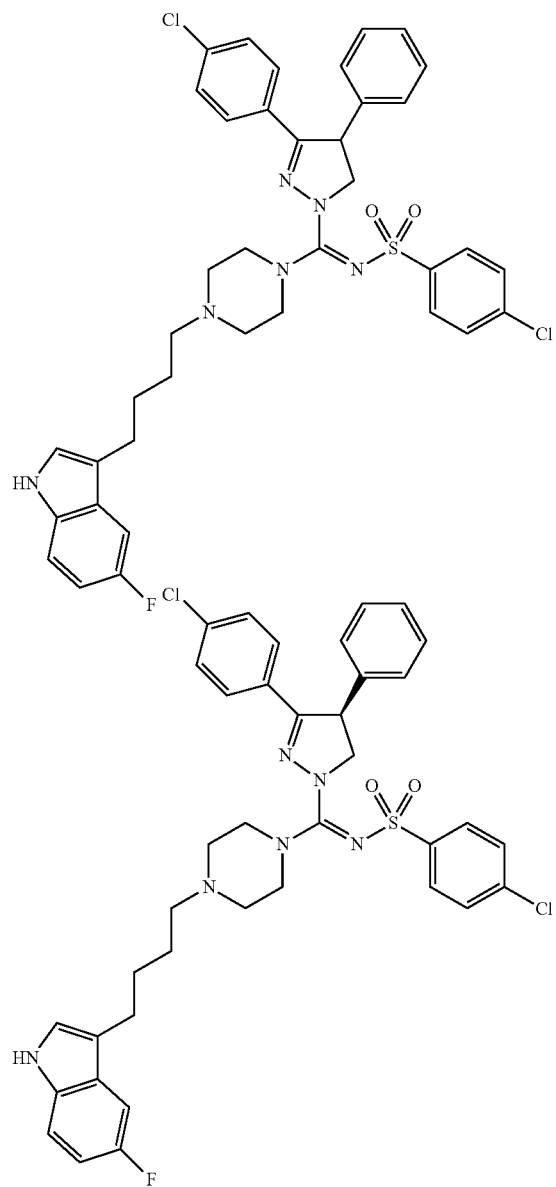
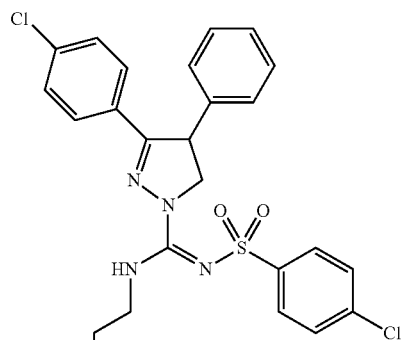
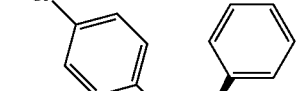

-continued

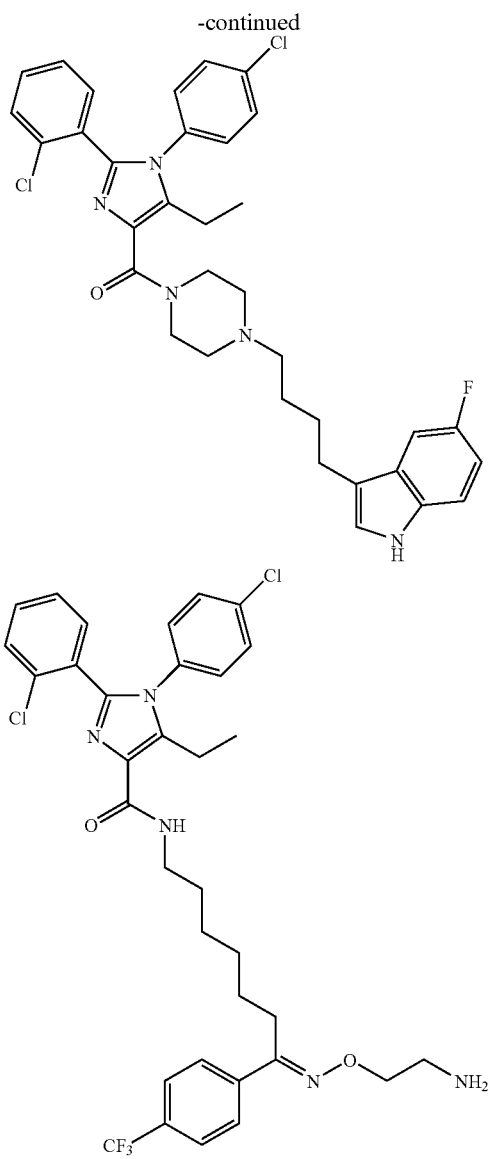

The compounds of the invention of the general formula (1), as well as the pharmacologically acceptable salts thereof, may have a combination of cannabinoid $CB_1$ antagonism and serotonin reuptake inhibition. They may be useful in the treatment of disorders in which cannabinoid $CB_1$ receptors and serotonin reuptake sites are involved, or that can be treated via manipulation of those receptors. For instance, compounds of the invention of the general formula (1) may be useful in the treatment of: addiction, alcoholism, Alzheimer's disease, anorexia nervosa, anxiety disorder, appetite disorders, attention deficit hyperactivity disorder, bipolar disorder, bulimia nervosa, cancer, cardiovascular disorders, central nervous system disease, cerebral ischaemia, cerebral apoplexy, chemotherapy induced emesis, cocaine addiction, cognitive disorder, dementia, demyelinisation related disorders, diabetes, diabetic neuropathy, diarrhea, drug dependence, dystonia, eating disorder, emesis, epilepsy, female sexual dysfunction, functional bowel disorder, gastrointestinal disorders, gastric ulcers, generalized anxiety disorder, glaucoma, headache, Huntington's disease, impulse control disorders inflammation, irritable bowel syndrome, male sexual dysfunction, major depressive disorder, memory disorders menopause, migraine, muscle spasticity, multiple sclerosis, myalgia, nausea, neuralgia, neurodegenerative disorders, neuroinflammatory disorders, neuropathic pain, obesity, obsessive compulsive disorder, osteoarthritis, pain, panic disorder, Parkinson's disease, plaque sclerosis, premature ejaculation, premenstrual syndrome, psychosexual disorder, psychosis, rheumatoid arthritis, septic shock, schizophrenia, sexual disorders, sleep disorder, spinal cord injury, stroke, Tourette's syndrome, traumatic brain injury, tremor, urinary incontinence, and viral encephalitis.

Other embodiments of the invention include, but are not limited to:

a pharmaceutical composition for treating, for example, a disorder or condition that may be treated by a combination of cannabinoid $CB_1$ antagonism and serotonin reuptake inhibition, the composition comprising a compound of formula (1) and a pharmaceutically acceptable carrier;

a method for treatment of a disorder or condition that may be treated by a combination of cannabinoid $CB_1$ antagonism and serotonin reuptake inhibition, the method comprising administering to a mammal in need of such treatment a compound of formula (1);

a pharmaceutical composition for treating, for example, a disorder or condition chosen from the disorders listed herein;

a method of treatment of a disorder or condition chosen from the disorders listed herein, the method comprising administering to a patient in need of such treatment a compound of formula (1);

a pharmaceutical composition for treating a disorder or condition chosen from the disorders listed herein, the composition comprising a compound of formula (1) and a pharmaceutically acceptable carrier;

a method for treating a disorder or condition chosen from the disorders listed herein, the method comprising administering to a patient in need of such treatment a compound of formula (1); and a method of antagonizing a cannabinoid $CB_1$ antagonism receptor and inhibiting serotonin reuptake, which comprises administering to a subject in need thereof, an effective amount of a compound of formula (1).

The invention also provides for the use of a compound according to formula (1) for the preparation of a medicament.

The invention further relates to combination therapies wherein a compound of the invention, or a pharmaceutical composition or formulation comprising a compound of the invention, is administered concurrently or sequentially or as a combined preparation with another therapeutic agent or agents, for the treatment of one or more of the conditions listed. Such other therapeutic agent(s) may be administered prior to, simultaneously with, or following the administration of the compounds of the invention.

The invention also provides compounds, pharmaceutical compositions, kits and methods for treating a disorder or condition chosen from the disorders listed herein, the method comprising administering to a patient in need of such treatment a compound of formula (1).

The compounds of the invention possess combination of cannabinoid $CB_1$ antagonism and serotonin reuptake inhibition. The (ant)agonizing/inhibiting activities of the compounds of the invention is readily demonstrated, for example, using one or more of the assays described herein or known in the art.

The invention also provides methods for preparing the compounds of the invention and the intermediates used in those methods.

Isolation and purification of the compounds and intermediates described herein can be affected, if desired, by any suitable separation or purification procedure such as, for example, filtration, extraction, crystallization, column chromatography, thin-layer chromatography, thick-layer chromatography, preparative low or high-pressure liquid chromatography, or a combination of these procedures. Specific illustrations of suitable separation and isolation procedures can be taken from the preparations and examples. However, other equivalent separation or isolation procedures could, of course, also be used.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula (1) shows the structure of the class of compounds without preferred stereochemistry. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base, such as for example (−)-di-p-toluoyl-D-tartaric acid and/or (+)-di-p-toluoyl-L-tartaric acid. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

Cis and trans isomers of the compounds of formula (1) or pharmaceutically acceptable salts thereof are also within the scope of the invention, and this also applies to tautomers of the compounds of formula (1) or pharmaceutically acceptable salts thereof.

Some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Isotopically-labeled compounds of formula (1) or pharmaceutically acceptable salts thereof, including compounds of formula (1) isotopically-labeled to be detectable by PET or SPECT, are also included within the scope of the invention, and same applies to compounds of formula (1) labeled with [$^{13}$C]—, [$^{14}$C]—, [$^{18}$F]—, [$^{3}$H]—, [$^{125}$I]— or other isotopically-enriched atoms, suitable for receptor binding or metabolism studies.

The compounds of the invention may also be used as reagents or standards in the biochemical study of neurological function, dysfunction and disease.

Definitions

Within the context of this description, the terms 'compound with cannabinoid $CB_1$ antagonism' and 'cannabinoid $CB_1$ antagonist' refer to compounds having this activity—measured by unambiguous and well accepted pharmacological assays, including those described herein—without displaying substantial cross-reactivity towards another receptor. In one embodiment, a compound of the present invention is at least 10 times more potent as a cannabinoid $CB_1$ antagonist than as an agonist or antagonist on any other receptor. In a further embodiment, compounds of the present invention are 100-fold more selective, and in a further embodiment, compounds of the present invention have a selectivity of a factor 1,000 or higher. The terms 'compound with serotonin reuptake inhibiting activity' or 'serotonin reuptake inhibitor' refer to a compounds having this activity—measured by unambiguous and well accepted pharmacological assays, including those described herein—without displaying substantial cross-reactivity towards another reuptake site. In one embodiment, a compound of the present invention is at least 10 times more potent as a serotonin reuptake inhibitor than as an inhibitor of the re-uptake of any other neurotransmitter. In a further embodiment, compounds of the present invention have a 100-fold selectivity, and in a further embodiment, compounds of the present invention have a selectivity of a factor 1,000 or more. A compound 'having both cannabinoid $CB_1$ antagonism and serotonin reuptake inhibitory activity', refers to compounds having both activities—measured by unambiguous and well accepted pharmacological assays, including those described herein—without displaying substantial cross-reactivity towards other receptors or reuptake sites. In one embodiment, a compound of the present invention is at least 10 times more potent as a cannabinoid $CB_1$ antagonist and as a serotonin reuptake inhibitor, than as an agonist or antagonist on any other receptor or as an inhibitor of any other reuptake site. In a further embodiment, compounds of the present invention have a 100-fold selectivity, and in a further embodiment, compounds of the present invention have a selectivity of a factor 1,000 or more.

General terms used in the description of compounds herein disclosed bear their usual meanings. The term alkyl as used herein denotes a univalent saturated, branched or straight, hydrocarbon chain. Unless otherwise stated, such chains can contain from 1 to 18 carbon atoms. Representative of such alkyl groups are methyl, ethyl, propyl, isopropyl, butyl, isobutyl, sec-butyl, tert-butyl, pentyl, isopentyl, neopentyl, tert-pentyl, hexyl, isohexyl, heptyl, octyl, nonyl, decyl, undecyl, dodecyl, tridecyl, tetradecyl, pentadecyl, hexadecyl, heptadecyl, octadecyl, and the like. When qualified 'lower', the alkyl group will contain from 1 to 6 carbon atoms. The same carbon content ($C_{1-18}$) applies to the parent term 'alkane', and to derivative terms such as 'alkoxy'. The carbon content of various hydrocarbon containing moieties is indicated by a prefix designating the minimum and maximum number of carbon atoms in the moiety, i.e., the prefix $C_x$-$C_y$ defines the number of carbon atoms present from the integer "x" to the integer "y" inclusive. 'Alkyl($C_{1-3}$)' for example, means methyl, ethyl, n-propyl or isopropyl, and 'alkyl($C_{1-4}$)' means 'methyl, ethyl, n-propyl, isopropyl, n-butyl, 2-butyl, isobutyl, or 2-methyl-n-propyl'.

The term 'acyl' means alkyl($C_{1-3}$)carbonyl, arylcarbonyl or aryl-alkyl($C_{1-3}$)carbonyl. 'Aryl' includes monocyclic or fused bicyclic aromatic or hetero-aromatic groups, including but not limited to furyl, thienyl, pyrrolyl, oxazolyl, thiazolyl, imidazolyl, imidazo[2,1-b][1,3]thiazolyl, pyrazolyl, isoxazolyl, isothiazolyl, pyridyl, pyridazinyl, pyrimidinyl, pyrazinyl, 1,3,5-triazinyl, phenyl, indazolyl, indolyl, indolizinyl, isoindolyl, benzo[b]furanyl, 1,2,3,4-tetrahydro-naphtyl, 1,2,3,4-tetrahydroisoquinolinyl, indanyl, indenyl, benzo[b] thienyl, 2,3-dihydro-1,4-benzodioxin-5-yl, benzimidazolyl, benzothiazolyl, benzo[1,2,5]thia-diazolyl, purinyl, quinolinyl, isoquinolinyl, phtalazinyl, quinazolinyl, quinoxalinyl, 1,8-naphthyridinyl, naphthyl, pteridinyl, and azulenyl. 'Halo' or 'Halogen' means chloro, fluoro, bromo or iodo; 'hetero' as in 'heteroalkyl,' 'heteroaromatic,' etc. means containing one or more N, O or S atoms. 'Heteroalkyl' includes alkyl groups with heteroatoms in any position, thus including N-bound, O-bound, or S-bound alkyl groups.

The term "substituted" means that the specified group or moiety bears one or more substituents. Where any group may carry multiple substituents, and a variety of possible substituents is provided, the substituents are independently chosen, and need not to be the same. The term "unsubstituted" means that the specified group bears no substituents. With reference to substituents, the term "independently" means that when more than one of such substituents are possible, they may be the same or different from each other.

The terms "oxy", "thio" and "carbo" as used herein as part of another group respectively refer to an oxygen atom, a sulphur atom and a carbonyl (C=O) group, serving as linker between two groups, such as for instance hydroxyl, oxyalkyl, thioalkyl, carboxyalkyl, etc. The term "amino" as used herein alone, or as part of another group, refers to a nitrogen atom that may be either terminal, or a linker between two other groups, wherein the group may be a primary, secondary or tertiary (two hydrogen atoms bonded to the nitrogen atom, one hydrogen atom bonded to the nitrogen atom and no hydrogen atoms bonded to the nitrogen atom, respectively) amine. The terms "sulfinyl" and "sulfonyl" as used herein as part of another group respectively refer to an —SO— or an —$SO_2$— group.

To provide a more concise description, the terms 'compound' or 'compounds' include tautomers, stereoisomers, N-oxides, isotopically-labelled analogues, pharmacologically acceptable salts, hydrates and solvates, also when not explicitly mentioned.

As used herein, the term "leaving group" (L) shall mean a charged or uncharged atom or group that departs during a substitution or displacement reaction. The term refers to groups readily displaceable by a nucleophile, such as an amine, a thiol or an alcohol nucleophile. Such leaving groups are well known in the art. Examples include, but are not limited to N-hydroxysuccinimide, N-hydroxybenzotriazole, halides (Br, Cl, I), triflates, mesylates, tosylates, and the like.

N-oxides of the compounds mentioned above belong to the invention. Tertiary amines may or may not give rise to N-oxide metabolites. The extent to what N-oxidation takes place varies from trace amounts to a near quantitative conversion. N-oxides may be more active than their corresponding tertiary amines, or less active. Whilst N-oxides can easily be reduced to their corresponding tertiary amines by chemical means, in the human body this happens to varying degrees. Some N-oxides undergo nearly quantitative reductive conversion to the corresponding tertiary amines, in other cases conversion is a mere trace reaction, or even completely absent (Bickel, 1969).

Any compound metabolized in vivo to provide the bioactive agent (i.e., the compound of formula (1)) is a prodrug within the scope and spirit of the application. Prodrugs are therapeutic agents, inactive per se but transformed into one or more active metabolites. Thus, in the methods of treatment of the present invention, the terms "administering" and "use in the treatment of" shall encompass treating the various disorders described with the compound specifically disclosed, or with a compound that is not specifically disclosed but that converts to the specified compound in vivo after administration to the patient. Prodrugs are bioreversible derivatives of drug molecules used to overcome some barriers to the utility of the parent drug molecule. These barriers include, but are not limited to, solubility, permeability, stability, presystemic metabolism, and targeting limitations (Bundgaard, 1985; King, 1994; Stella, 2004; Ettmayer, 2004; Järvinen, 2005). Prodrugs, i.e., compounds that when administered to humans or mammals by any known route are metabolized to compounds of formula (1), belong to the invention. In at least one embodiment, this relates to compounds with primary or secondary amino groups or hydroxy groups. Such compounds can be reacted with organic acids to yield compounds of formula (1) wherein an additional group is present that is easily removed after administration, for instance, but not limited to amidine, enamine, a Mannich base, a hydroxylmethylene derivative, an O-(acyloxymethylene carbamate) derivative, carbamate, ester, amide, or enaminone.

'Crystal form' refers to various solid forms of the same compound, for example polymorphs, solvates, and amorphous forms. 'Polymorphs' are crystal structures in which a compound can crystallize in different crystal packing arrangements, all of which have the same elemental composition. Polymorphism is a frequently occurring phenomenon, affected by several crystallization conditions such as temperature, level of supersaturation, the presence of impurities, polarity of solvent, and rate of cooling. Different polymorphs usually have different X-ray diffraction patterns, solid state NMR spectra, infrared or Raman spectra, melting points, density, hardness, crystal shape, optical and electrical properties, stability, and solubility. Recrystallization solvent, rate of crystallization, storage temperature, and other factors may cause one crystal form to dominate. 'Solvates' are generally a crystal form that contains either stoichiometric or non-stoichiometric amounts of a solvent. Often, during the process of crystallization some compounds have a tendency to trap a fixed molar ratio of solvent molecules in the crystalline solid state, thus forming a solvate. When the solvate is water, 'hydrates' may be formed. The compounds of formula (1) and pharmaceutically acceptable salts thereof may exist in the form of a hydrate or a solvate, and such a hydrate and solvate are also encompassed in the present invention. Examples thereof include ¼ hydrate, dihydrochloride dihydrate, and the like. 'Amorphous' forms are noncrystalline materials with no long range order, and generally do not give a distinctive powder X-ray diffraction pattern. Crystal forms in general have been described by Byrn (1995) and Martin (1995).

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

Throughout the description and the claims of this specification, the word "comprise" and variations of the word, such as "comprising" and "comprises," are not intended to exclude other additives, components, integers or steps.

While it may be possible for the compounds of formula (1) to be administered as the raw chemical, in at least one embodiment, they are presented in a 'pharmaceutical composition'. According to a further aspect, the present invention provides a pharmaceutical composition comprising at least one compound of formula (1), at least one pharmaceutically acceptable salt or solvate thereof, or a mixture of any of the foregoing, together with one or more pharmaceutically acceptable carriers thereof, and optionally one or more other therapeutic ingredients. The at least one carrier must be 'acceptable' in the sense of being compatible with the other ingredients of the formulation and not deleterious to the recipient thereof. The term "composition" as used herein encompasses a product comprising specified ingredients in predetermined amounts or proportions, as well as any product that results, directly or indirectly, from combining specified ingredients in specified amounts. In relation to pharmaceutical compositions, this term encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. The pharmaceutical composition includes enough of the active object compound to produce the desired effect upon the progress or condition of diseases. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The affinity of the compounds of the invention for $CB_1$ receptors and 5-HT reuptake sites was determined as described below. From the binding affinity measured for a given compound of formula (1), one can estimate a theoretical lowest effective dose. At a concentration of the compound equal to twice the measured $K_i$-value, nearly 100% of the $CB_1$ receptors likely will be occupied by the compound. By converting that concentration to mg of compound per kg of patient one obtains a theoretical lowest effective dose, assuming ideal bioavailability. Pharmacokinetic, pharmacodynamic, and other considerations may alter the dose actually administered to a higher or lower value. The dose of the compound to be administered will depend on the relevant indication, the age, weight and sex of the patient and may be determined by a physician. The dosage will, in at least one embodiment, be in the range of from 0.01 mg/kg to 10 mg/kg. The typical daily dose of the active ingredients varies within a wide range and will depend on various factors such as the relevant indication, the route of administration, the age, weight and sex of the patient, and may be determined by a physician. In general, total daily dose administration to a patient in single or individual doses, may be in amounts, for example, from 0.001 to 10 mg/kg body weight daily, and more usually from 0.01 to 1,000 mg per day, of total active ingredients. Such dosages will be administered to a patient in need of treatment from one to three times each day, or as often as needed for efficacy, and for periods of at least two months, more typically for at least six months, or chronically.

The term "therapeutically effective amount" as used herein refers to an amount of a therapeutic agent to treat a condition treatable by administrating a composition of the invention. That amount is the amount sufficient to exhibit a detectable therapeutic or ameliorative response in a tissue system, animal or human. The effect may include, for example, treating the conditions listed herein. The precise effective amount for a subject will depend upon the subject's size and health, the nature and extent of the condition being treated, recommendations of the treating physician (researcher, veterinarian, medical doctor or other clinician), and the therapeutics, or combination of therapeutics, chosen for administration. Thus, it is not useful to specify an exact effective amount in advance. The term "pharmaceutically acceptable salt" refers to those salts that are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. They can be prepared in situ when finally isolating and purifying the compounds of the invention, or separately by reacting them with pharmaceutically acceptable non-toxic bases or acids, including inorganic or organic bases and inorganic or organic acids (Berge, 1977). The 'free base' form may be regenerated by contacting the salt with a base or acid, and isolating the parent compound in the conventional matter. The parent form of the compound may differ from the various salt forms in certain physical properties, such as solubility in polar solvents, but otherwise the salts should be equivalent to the parent form of the compound for the purposes of the present invention. 'Complex' refers to a complex of the compound of the invention, e.g. formula (1), complexed with a metal ion, where at least one metal atom is chelated or sequestered. Complexes are prepared by methods well known in the art (Dwyer, 1964).

The term "treatment" as used herein refers to any treatment of a mammalian, for example human, condition or disease, and includes: (1) inhibiting the disease or condition, i.e., arresting its development, (2) relieving the disease or condition, i.e., causing the condition to regress, or (3) stopping the symptoms of the disease. The term 'inhibit' includes its generally accepted meaning which includes prohibiting, preventing, restraining, alleviating, ameliorating, and slowing, stopping or reversing progression, severity, or a resultant symptom. As such, the present method includes both medical therapeutic and/or prophylactic administration, as appropriate. As used herein, the term "medical therapy" is intended to include prophylactic, diagnostic and therapeutic regimens carried out in vivo or ex vivo on humans or other mammals. 'Mammals' include animals of economic importance such as bovine, ovine, and porcine animals, especially those that produce meat, as well as domestic animals, sports animals, zoo animals, and in at least one embodiment, humans. The term "subject" as used herein, refers to an animal, in at least one embodiment, a mammal, for example a human, who has been the object of treatment, observation or experiment.

Abbreviations
BOC tert-butoxycarbonyl
BOP benzotriazol-1-yl-oxytris-phosphonium hexafluorophosphate
$CB_1$ cannabinoid receptor subtype-1
$CB_2$ cannabinoid receptor subtype-2
CHO Chinese Hamster Ovary (cells)
CIP 2-chloro-1,3-dimethylimidazolinium hexafluorophosphate DCC dicyclohexylcarbodiimide
DIPEA diisopropylethylamine
DMAP 4-dimethylaminopyridin
DMSO dimethylsulfoxide
EDCl 1-(3-dimethylaminopropyl)-3-ethylcarbodiimide hydrochloride
HBTU O-benzotriazol-1-yl-N,N,N',N'-tetramethyluronium hexafluorophosphate
HOAt N-hydroxy-7-azabenzotriazole
mg milligram(s)
min minute(s)
PET positron emission tomography
PyAOP 7-azabenzotriazol-1-yloxytris(pyrrolidino)-phosphonium hexafluorophosphate
PyBOP benzotriazol-1-yloxytris(pyrrolidino)-phosphonium hexafluorophosphate
$R_f$ retention factor (thin layer chromatography)
SPECT single photon emission computed tomography
(S)SRI (selective) serotonin reuptake inhibitor
TBTU O-(Benzotriazol-1-yl)-N,N,N',N'-tetramethyluronium tetrafluoroborate
THF tetrahydrofuran

EXAMPLES

Example 1

Analytical Methods

Nuclear magnetic resonance spectra ($^1$H NMR and $^{13}$C NMR, APT) were determined in the indicated solvent using a Bruker ARX 400 ($^1$H: 400 MHz, $^{13}$C: 100 MHz) at 300 K, or a Bruker (300 MHz) unless indicated otherwise. The spectra were determined in deuterated chloroform or DMSO-$d_6$ obtained from Cambridge Isotope Laboratories Ltd. Chemical shifts (δ) are given in ppm downfield from tetramethylsilane ($^1$H, $^{13}$C) or CCl$_3$F ($^{19}$F). Coupling constants J are given in Hz. Peakshapes in the NMR spectra are indicated with the symbols 'q' (quartet), 'dq' (double quartet), 't' (triplet), 'dt' (double triplet), 'd' (doublet), 'dd' (double doublet), 's' (singlet), 'br s' (broad singlet) and 'm' (multiplet).

Flash chromatography/column chromatography refers to purification using the indicated eluent and silica gel (either Acros: 0.030-0.075 mm or Merck silica gel 60: 0.040-0.063 mm) or if specifically stated Alumina: 'Aluminumoxide Fluka for Chromatography'; pH=9.5; 0.05-0.15 mm.

Thin layer chromatography (TLC) was performed on Merck Kieselgel 60 F$_{254}$ plates 20×20 cm.

Melting points were recorded on a Büchi B545 melting point apparatus.

All reactions involving moisture sensitive compounds or conditions were carried out under an anhydrous nitrogen atmosphere.

Reactions were monitored by using thin-layer chromatography on silica coated plastic sheets (Merck precoated silica gel 60 F$_{254}$) with the indicated eluent. Spots were visualized by UV light (254 nm) or I$_2$.

Dichloromethane (phosphorous pentoxide and calciumhydride), tetrahydrofuran (sodium/benzophenone ketyl) and light petroleum (60-80) were distilled freshly prior to use. All other commercially available chemicals were used without further purification.

Example 2

General Aspects of Syntheses

The syntheses of the structural components of known cannabinoid CB$_1$ antagonist are described in patent applications and/or scientific literature. For instance, well-documented are the essential cannabinoid structural components ($A^{1a}$) (WO01070700, Lange, 2004b), ($A^{1b}$) (WO03026648), ($A^2$) (WO03027076, WO03040107, WO03063781, Lange, 2005b; Dyck, 2004), ($A^3$) (EP0576357, EP1150961, Lan, 1999; Seltzman, 1995; Dutta, 1994 and Katoch-Rouse, 2003), ($A^4$) (WO03007887, Plummer, 2005), ($A^5$) (WO0307069), ($A^6$) (WO03078413, Lange, 2005b), ($A^7$) (WO2004026301, Lange, 2005b; Dyck, 2004) and ($A^8$) (WO2004013120).

In general terms, the synthesis of compounds of formula (1) wherein R is a hydrogen atom can be accomplished by reacting a compound of general formula A-L wherein L is a leaving group with a compound of general formula HRN-TB. It will be apparent for those skilled in the art that the amino group present in HRN-TB must be sufficiently nucleophilic in order to displace the leaving group from A-L in such a reaction. In the case that L is a hydroxy group which is part of a carboxylic acid group, activating or coupling reagents may be added in order to enhance the reaction rate (Bodanszky, 1994; Akaji, 1994; Albericio, 1997; Montalbetti, 2005).

The synthesis of compounds of the general formula (1) wherein A is a cannabinoid structural component chosen from structures ($A^{1a}$) and ($A^{1b}$) wherein $R^1$, $R^2$ and $R^3$ independently are chosen from hydrogen atoms, trifluoromethyl groups, and halogen atoms, is outlined in Scheme 3.

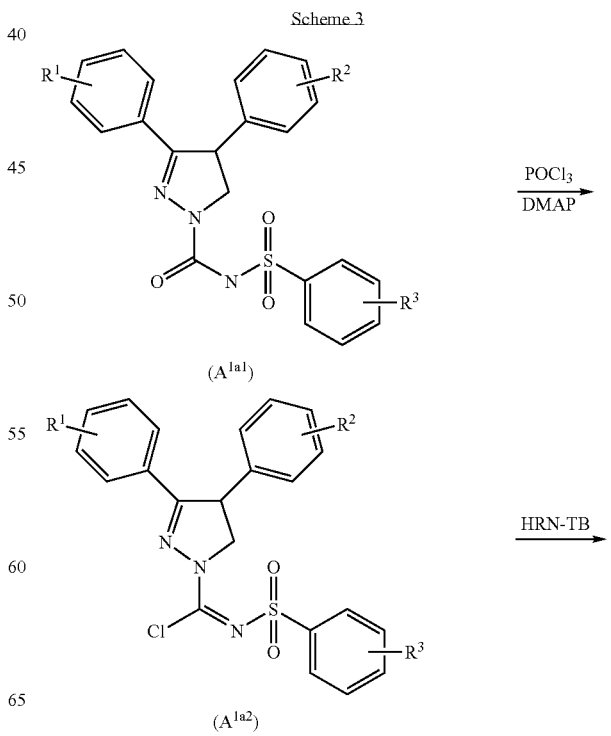

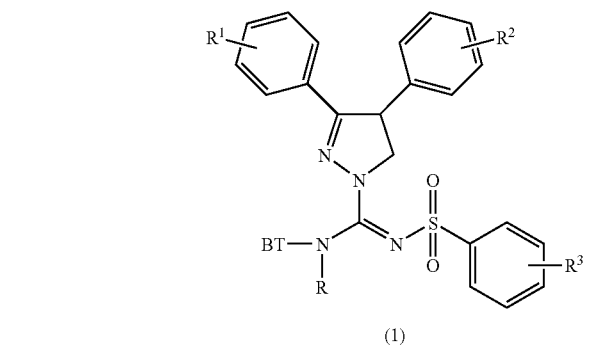

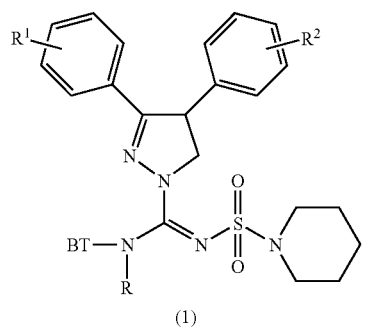

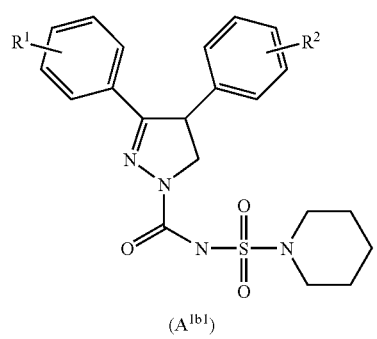

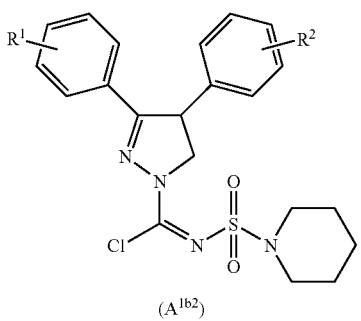

A compound of general formula ($A^{1a1}$) can be reacted with POCl$_3$ in the presence of DMAP in an inert organic solvent such as dichloromethane to give the corresponding derivative of general formula ($A^{1a2}$). This compound of general formula ($A^{1a2}$) can be reacted with a compound of general formula HRN-TB. This reaction can give a compound of general formula (1) wherein A is ($A^{1a}$) and wherein R, N, T and B have the abovementioned meaning. Analogously, a compound of general formula ($A^{1b1}$) can be reacted with POCl$_3$ in the presence of DMAP in an inert organic solvent such as dichloromethane to give the corresponding chloride derivative of general formula ($A^{1b2}$). This compound of general formula ($A^{1b2}$) can be reacted with a compound of general formula HRN-TB. This reaction can give a compound of general formula (1) wherein A is ($A^{1b}$) and wherein R, N, T and B have the abovementioned meaning.

The synthesis of compounds of the general formula (1) wherein A is the cannabinoid structural component of structure ($A^2$) is outlined in Scheme 4.

Scheme 4

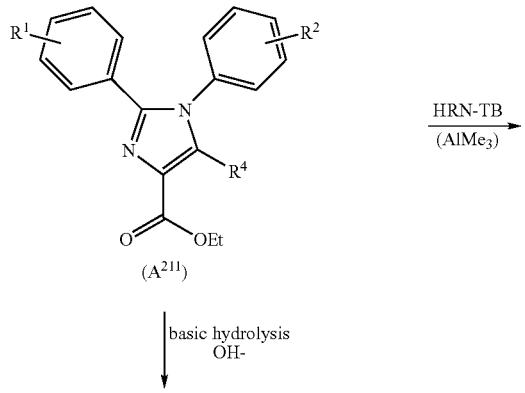

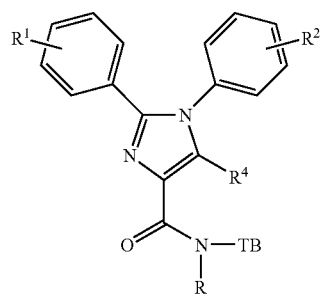

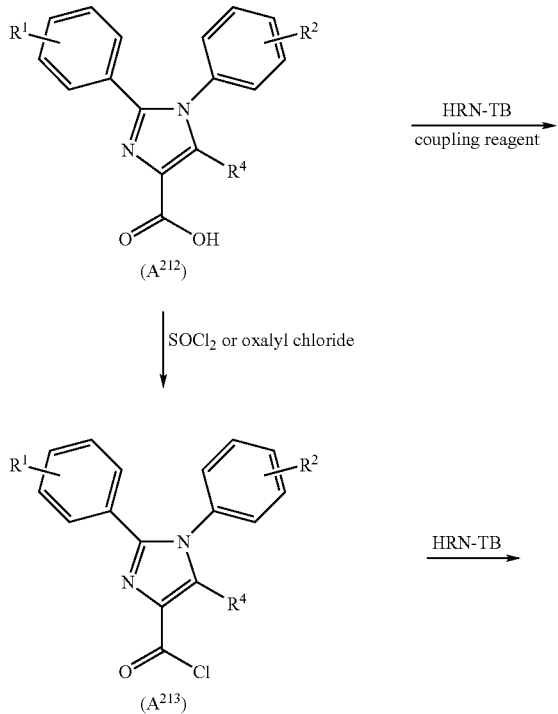
(A²¹²)

HRN-TB coupling reagent →

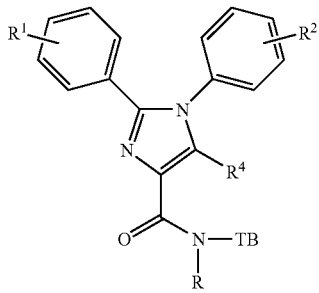
(1) wherein A is derived from A²

↓ SOCl₂ or oxalyl chloride

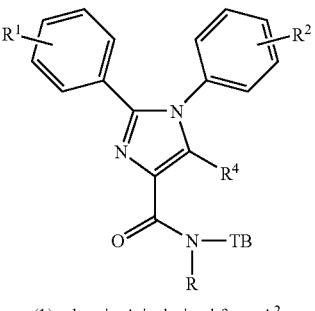
(A²¹³)

HRN-TB →

(1) wherein A is derived from A²

In Scheme 4, R¹ and R² independently are chosen from a hydrogen atom, a trifluoromethyl group, and halogen atoms, R⁴ is chosen from a hydrogen atom, halogen atoms, methyl, ethyl, trifluoromethyl, hydroxymethyl, fluoromethyl, 2,2,2-trifluoroethyl, propyl, methylsulfanyl, methyl-sulfinyl, methylsulfonyl, ethylsulfanyl, ethylsulfinyl, ethylsulfonyl, C1-3-dialkyl-aminomethyl, pyrrolidin-1-ylmethyl, piperidin-1-ylmethyl, and morpholin-4-ylmethyl, and the other substituents have the definitions as given above.

An ester of general formula (A²ⁱ¹) can be reacted with a compound of general formula HRN-TB to give a compound of general formula (1) wherein part A is derived from substructure A². Such a reaction can be catalyzed by trimethylaluminum (AlMe₃) (Levin, 1982).

Alternatively, a compound of general formula (A²ⁱ¹) can be hydrolyzed into the corresponding carboxylic acid of general formula (A²ⁱ²). A compound of general formula (A²ⁱ²) can be reacted with a compound of general formula HRN-TB to give a compound of general formula (1) wherein part A is derived from substructure A². This reaction, in at least one embodiment, proceeds via activating and coupling methods such as formation of an active ester, or in the presence of a so-called coupling reagent, for example, DCC, HBTU, TBTU, HOAt, PyBOP, BOP, CIP, 2-chloro-1,3-dimethyl-imidazolinium chloride, PyAOP and the like.

Alternatively, a compound of general formula (A²ⁱ²) can be converted in the presence of a chlorinating agent such as thionyl chloride or oxalyl chloride into the corresponding acid chloride of general formula (A²ⁱ³). A compound of general formula (A²ⁱ³) can be reacted with a compound of general formula HRN-TB to give a compound of general formula (1) wherein A is derived from substructure A². A base like DIPEA can be added to the reaction mixture to scavenge the liberated hydrochloric acid or excess HRN-TB can be applied for this purpose.

Analogously, the substructures of general formula (A³) (A⁴), (A⁵), (A⁶), (A⁷), or (A⁸), as given above, can be converted into compounds of the general formula (1) wherein A is derived from the substructures (A³) (A⁴), (A⁵), (A⁶), (A⁷), or (A⁸) respectively.

The selection of the particular synthetic procedures depends on factors known to those skilled in the art, such as the compatibility of functional groups with the reagents used, the possibility to use protecting groups, catalysts, activating and coupling reagents, and the ultimate structural features present in the final compound being prepared.

Pharmaceutically acceptable salts may be obtained using standard procedures well known in the art, for example by mixing a compound of the present invention with a suitable acid, for instance an inorganic acid or an organic acid.

Example 3

Synthesis of Intermediates

Intermediate A: 4-chloro-1-(5-fluoro-1H-indol-3-yl)-butan-1-one

Intermediate A

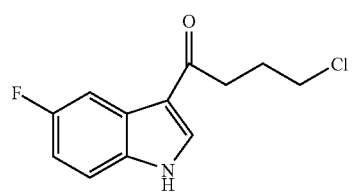

To a magnetically stirred mixture of AlCl₃ (25 g, 0.19 mol) in dichloromethane, 4-chloro-butyryl chloride (21 ml, 0.19 mol) was slowly added at 0° C. The resulting mixture was stirred for 30 minutes and 5-fluoro-1H-indole (25 g, 0.19 mol) was slowly added. After stirring for another 30 minutes the formed orange mixture was poured onto concentrated hydrochloric acid (140 ml) and ice (200 ml) to give a pink precipitate. The precipitate was collected by filtration to give pink 4-chloro-1-(5-fluoro-1H-indol-3-yl)-butan-1-one (29 gram, 65% yield). $^1$H-NMR (400 MHz, DMSO-$d_6$) δ 2.09 (quintet, J=7, 2H), 3.02 (t, J=7, 2H), 3.70 (t, J=7, 2H), 7.07 (dt, J~9 and 2, 1H), 7.49 (dd, J~9 and 4, 1H), 7.85 (dd, J~9 and 2, 1H), 8.41 (d, J~3, 1H), 12.21 (br s, 1H).

Intermediate B: 4-[4-(5-fluoro-1H-indol-3-yl)-4-oxobutyl]-piperazine-1-carboxylic acid tert-butyl ester Intermediate B

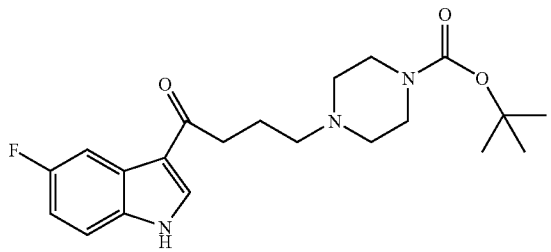

To a magnetically stirred solution of 4-chloro-1-(5-fluoro-1H-indol-3-yl)-butan-1-one (10.93 g, 45.6 mmol) in acetonitrile (100 ml), piperazine (20.33 g ml, 236 mmol) and a small amount of potassium iodide (0.1 g) were added, and the resulting mixture was heated at 80° C. for 48 hours. The formed solid material was removed by filtration and the residue was concentrated in vacuo to give 37 g crude yield. This crude product was further purified by column chromatography (gradient: ethylacetate/methanol/25% aqueous ammonia=90/5/5 to methanol) to give 17.1 g crude 1-(5-fluoro-1H-indol-3-yl)-4-(piperazin-1-yl)-butan-1-one. Then this crude 1-(5-fluoro-1H-indol-3-yl)-4-(piperazin-1-yl)-butan-1 -one (10.71 g, 0.389 mol) was dissolved in dichloromethane (500 ml) and Boc$_2$O (25.53 g, 0.117 mol) was added. The resulting mixture was stirred for 4 hours at room temperature. The mixture was successively washed with 5% aqueous NaHCO$_3$ and water. The organic layer was dried over Na$_2$SO$_4$, filtered and concentrated in vacuo. Subsequent column chromatography (gradient: dichloro-methane/methanol=99/1 to dichloro-methane/methanol=90/10 (v/v)) gave pure 4-[4-(5-fluoro-1H-indol-3-yl)-4-oxobutyl]-piperazine-1-carboxylic acid tert-butyl ester (3.85 g, 37% yield). $^1$H-NMR (400 MHz, DMSO-$d_6$) δ 1.38 (s, 9H), 1.80 (quintet, J=7, 2H), 2.25-2.35 (m, 6H), 2.84 (t, J=7, 2H), 3.22-3.32 (m, 4H), 7.06 (dt, J~9 and 3, 1H), 7.47 (dd, J~9 and 5, 1H), 7.85 (dd, J~9 and 3, 1H), 8.38 (s, 1H), 12.01 (brs, 1H).

Intermediate C: 5-fluoro-3-[4-(piperazin-1-yl)butyl]-1H-indole

Intermediate C

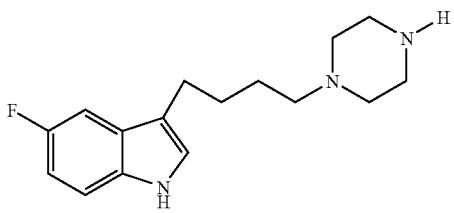

To a magnetically stirred solution of 4-[4-(5-fluoro-1H-indol-3-yl)-4-oxobutyl]-piperazine-1-carboxylic acid tert-butyl ester (3.85 g, 9.88 mmol) in dichloromethane was added hydrochloric acid (dissolved in dioxane: 4.94 ml, 4M solution, 19.8 mmol HCl) and the resulting mixture was reacted at room temperature for 4 hours. The reaction mixture was thoroughly concentrated in vacuo to give 1-(5-fluoro-1H-indol-3-yl)-4-(piperazin-1-yl)butan-1-one dihydrochloride (3.20 g). Some characteristic $^1$H-NMR signals from 1-(5-fluoro-1H-indol-3-yl)-4-(piperazin-1-yl)butan-1-one dihydrochloride are: (400 MHz, DMSO-$d_6$) δ 2.07 (quintet, J=7, 2H), 3.03 (t, J=7, 2H), 7.08 (dt, J~9 and 3, 1H), 7.50 (dd, J~9 and 4, 1H), 7.85 (dd, j~9 and 3, 1H), 8.43 (d, J~3, 1H), 12.21 (br s, 1H).

The obtained 1-(5-fluoro-1H-indol-3-yl)-4-(piperazin-1-yl)butan-1-one dihydrochloride (3.20 g) was dissolved in tetrahydrofuran (50 ml) and cooled to 0° C. A solution of LiAlH$_4$ in tetrahydrofuran (60 ml; 1M, ~53 mmol LiAlH$_4$) was slowly added. Subsequently, the mixture was heated at 80° C. for 20 hours. The excess LiAlH$_4$ was cautiously hydrolyzed and after extractive work-up, 5-fluoro-3-[4-(piperazin-1-yl)butyl]-1H-indole (2.39 g, 98% yield) was obtained. $^1$H-NMR (400 MHz, DMSO-$d_6$) δ 1.40-1.50 (m, 2H), 1.61 (quintet, J=7, 2H), 2.12-2.35 (m, 7H), 2.60-2.70 (m, 6H), 6.85-6.92 (m, 1H), 7.17 (d, J~2, 1H), 7.23 (dd, J~9 and 2, 1H), 7.30 (dd, J~9 and 4, 1H), 10.85 (br s, 1H).

Intermediate D: 7-(tetrahydropyran-2-yloxy)-1-[4-(trifluoromethyl)phenyl]heptan-1-one Intermediate D

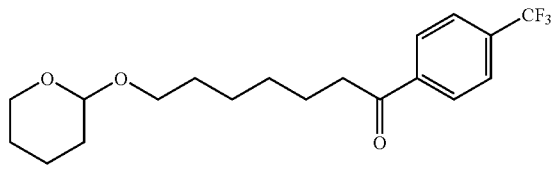

Magnesium (1.20 g, 0.0494 mol) was added to anhydrous THF (5 ml) and, at reflux temperature, 1,2-dibromoethane (1 ml), a small crystal of iodine and 2-(6-chlorohexyloxy)tetrahydro-2-pyran (10.0 g, 0.0453 mol; dissolved in 9 ml of THF) were successively added. The resulting mixture was heated at reflux temperature for 30 minutes. 4-Trifluoromethylbenzonitrile (7.0 g, 0.0412 mol: dissolved in 8 ml toluene) was slowly added and the mixture was heated for another 30 minutes. The mixture was allowed to attain room temperature and quenched with acetic acid (30 ml). The organic layer was separated and successively washed with water, 5% aqueous NaHCO$_3$, water (twice) and brine. The organic layer was dried over Na$_2$SO$_4$, filtered and concentrated in vacuo. Subsequent column chromatography (ethylacetate/heptane=10/90 (v/v)) gave pure 7-(tetrahydropyran-2-yloxy)-1-[4-(trifluoromethyl)phenyl]heptan-1-one (10.92 g, 74%) as an oil. R$_f$=0.25 (ethylacetate/heptane=⅙ (v/v). $^1$H-NMR (400 MHz, CDCl$_3$) δ 1.39-1.88 (m, 14H), 3.00 (t, J=7, 2H), 3.36-3.43 (m, 1H), 3.47-3.52 (m, 1H), 3.71-3.77 (m, 1H), 3.83-3.90 (m, 1H), 4.56-4.58 (m, 1H), 7.73 (d, J~8, 2H), 8.06 (d, J~8, 2H).

Intermediate E: toluene-4-sulfonic acid 7-oxo-7-[4-(trifluoromethyl)phenyl]heptyl ester Intermediate E

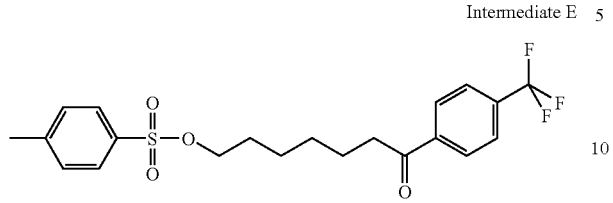

To a magnetically stirred solution of 7-(tetrahydropyran-2-yloxy)-1-[4-(trifluoromethyl)phenyl]heptan-1-one (7.70 g, 0.0215 mol) in methanol (50 ml) was added para-toluenesulfonic acid hydrate (4.18 g, 0.022 mol). The resulting acidic mixture (pH~2, pH paper) was reacted at room temperature for 20 hours. NaOH (1N) was added until the solution was neutral (pH~7, pH paper) and the resulting mixture was concentrated in vacuo. NaOH (1N, 50 ml) was added and the mixture was extracted with dichloromethane (3×). The combined organic layers were successively washed with water and brine. The organic layer was dried over Na$_2$SO$_4$, filtered and concentrated in vacuo to give crude 7-hydroxy-1-[4-(trifluoromethyl)phenyl]heptan-1-one (5.85 g, 99% yield) as a white solid. This obtained solid was treated with pyridine (29.6 ml) and a solution of tosyl chloride (17.72 g, 0.093 mol) in pyridine (89 ml) was added at 0° C. The mixture was allowed to attain room temperature and reacted for 1 hour. The mixture was cooled at −10° C. and quenched with excess water. Extraction with diethyl ether (3×), followed by drying over Na$_2$SO$_4$, filtering and concentration in vacuo gave crude product which was purified by column chromatography (dichloromethane/heptane=2/1 (v/v)) to give pure toluene-4-sulfonic acid 7-oxo-7-[4-(trifluoromethyl)phenyl]heptyl ester (7.91 g, 87% yield). $^1$H-NMR (400 MHz, CDCl$_3$) δ 1.35-1.38 (m, 4H), 1.57-1.73 (m, 4H), 2.44 (s, 3H), 2.97 (t, J=7, 2H), 4.03 (t, J=7, 2H), 7.35 (d, J~8, 2H), 7.73 (d, J~8, 2H), 7.79 (d, J~8, 2H), 8.04 (d, J~8, 2H).

Intermediate F: toluene-4-sulfonic acid 7,7-dimethoxy-7-[4-(trifluoromethyl)phenyl]heptyl ester Intermediate F

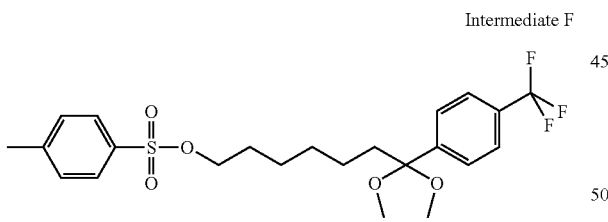

To a magnetically stirred solution of toluene-4-sulfonic acid 7-oxo-7-[4-(trifluoromethyl)phenyl]heptyl ester (2.77 g, 6.464 mmol) in methanol (75 ml), a catalytic amount of para-toluenesulfonic acid (0.097 g, 0.508 mmol) and excess trimethylorthoformate (16 ml, 142 mmol) were successively added. The resulting mixture was heated at reflux temperature for 20 hours. After allowing the reaction mixture to attain room temperature saturated aqueous NaHCO$_3$ and dichloromethane were successively added. The separated organic layer was washed with saturated aqueous NaHCO$_3$. The organic layer was subsequently dried over Na$_2$SO$_4$, filtered and concentrated in vacuo to give crude toluene-4-sulfonic acid 7,7-dimethoxy-7-[4-(trifluoromethyl)phenyl]heptyl ester which was purified by column chromatography (alumina, ethylacetate/heptane=1/10 (v/v)) to give pure toluene-4-sulfonic acid 7,7-dimethoxy-7-[4-(trifluoromethyl)phenyl] heptyl ester (1.82 g, 59% yield). $^1$H-NMR (400 MHz, CDCl$_3$) δ 0.84-0.93 (m, 2H), 1.06-1.26 (m, 4H), 1.51-1.57 (m, 2H), 1.80-1.86 (m, 2H), 2.44 (s, 3H), 3.13 (s, 6H), 3.94 (t, J=7, 2H), 7.32 (d, J~8, 2H), 7.55 (d, J~8, 2H), 7.60 (d, J~8, 2H), 7.75 (d, J~8, 2H).

Intermediate G: 7,7-dimethoxy-7-[4-(trifluoromethyl)phenyl]heptylamine

Intermediate G

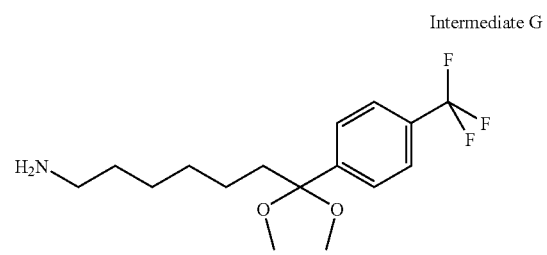

Toluene-4-sulfonic acid 7,7-dimethoxy-7-[4-(trifluoromethyl)phenyl]heptyl ester (1.82 g, 3.835 mmol) was dissolved in a magnetically stirred solution of 7 M NH$_3$ in methanol (30 ml) and stirred at room temperature for 72 hours. After removal of the solvent in vacuo, the residue was dissolved again in dichloromethane and washed with saturated aqueous NaHCO$_3$. The organic layer was subsequently dried over Na$_2$SO$_4$, filtered and concentrated in vacuo to give crude 7,7-dimethoxy-7-[4-(trifluoromethyl)phenyl]heptylamine (1.43 g) which was not further purified. $^1$H-NMR (400 MHz, CDCl$_3$) δ 0.88-0.95 (m, 2H), 1.12-1.16 (m, 4H), 1.33-1.38 (m, 2H), 1.83-1.88 (m, 2H), 2.59-2.65 (m, 2H), 3.10-3.26 (m, 8H, including —OMe singlet at 3.14), 7.56 (d, J~8, 2H), 7.60 (d, J~8, 2H).

Example 4

Syntheses of Specific Compounds

The specific compounds of which the synthesis is described below are intended to further illustrate the invention in more detail, and therefore are not deemed to restrict the scope of the invention in any way. Other embodiments of the invention will be apparent to those skilled in the art from consideration of the specification and practice of the invention disclosed herein. It is thus intended that the specification and examples be considered as exemplary only.

N-{1-[7-(2-amino-ethoxyimino)-7-[4-(trifluoromethyl)phenyl]heptylamino]-1-[3-(4-chlorophenyl)-4-phenyl-4,5-dihydro-1H-pyrazol- 1 -yl]-methylidene)}-4-chloro-benzenesulfonamide (Compound 1)

Compound 1

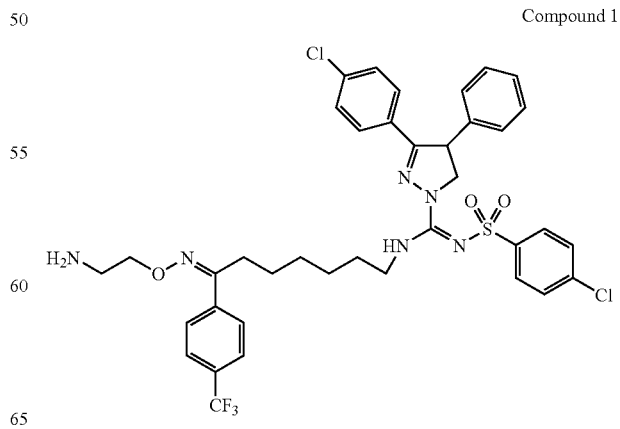

Part A: 3-(4-Chlorophenyl)-N-[(4-chlorophenyl)sulfonyl]-4-phenyl-4,5-dihydro-1H-pyrazole-1-carboxamide was obtained as described (Lange, 2004b). 3-(4-Chloro-phenyl)-N-[(4-chloro-phenyl)sulfonyl]-4-phenyl-4,5-dihydro-1H-pyrazole-1-carboxamid (0.708 g, 1.493 mol) was dissolved in anhydrous dichloromethane (15 ml) and DMAP (0.820 g, 6.716 mmol) and $POCl_3$ (0.209 g, 2.238 mmol) were successively added and the resulting mixture was refluxed for 5 hours. The mixture was cooled at 0° C. 7,7-Dimethoxy-7-[4-(trifluoromethyl)phenyl]-heptylamine (1.43 g, 4.477 mmol) and DIPEA (0.740 ml, 4.48 mmol) were successively added. The mixture was subsequently heated at reflux temperature for 30 hours. The mixture was allowed to attain room temperature and was washed with 5% aqueous $NaHCO_3$, dried over $Na_2SO_4$, filtered and concentrated in vacuo. The obtained crude product was purified by column chromatography (alumina; gradient: heptane/ethylacetate=6/1 to ethylacetate to ethylacetate/methanol=95/5 (v/v)) to give pure 4-chloro-N-{[3-(4-chlorophenyl)-4-phenyl-4,5-dihydro-1H-pyrazol-1-yl]-[7-(4-fluorophenyl)-7,7-dimethoxyheptylamino] methylene}benzenesul fonamide (0.200 g, 17% yield). $^1$H-NMR (400 MHz, $CDCl_3$) δ 60.91-1.01 (m, 2H), 1.17-1.28 (m, 4H), 1.49-1.57 (m, 2H), 1.85-1.92 (m, 2H), 3.15 (s, 6H), 3.50-3.58 (m, 2H), 4.04-4.13 (m, 1H), 4.47-4.65 (m, 2H), 7.10 (d, J~8, 2H), 7.22-7.32 (m, 5H) 7.35 (d, J~8, 2H), 7.48 (d, J~8, 2H), 7.58 (d, J~8, 2H), 7.61 (d, J~8, 2H), 7.82 (d, J~8, 2H), invisible NH proton.

Part B: 4-Chloro-N-{[3-(4-chlorophenyl)-4-phenyl-4,5-dihydro-1H-pyrazol-1-yl]-[7-(4-fluoro-phenyl)-7,7-dimethoxyheptylamino] methylene}-benzenesulfonamide (0.200 g, 0.258 mmol) was dissolved in a 1:1 mixture of THF/methanol (30 ml) and 1 N hydrochloric acid (5 ml) was added and the resulting mixture was stirred at room temperature for 20 hours. The mixture was quenched with 5% aqueous $NaHCO_3$. Most of the THF and methanol were removed by evaporation in vacuo. The remaining water layer was twice extracted with ethylacetate. The combined organic layers were dried over $Na_2SO_4$, filtered and concentrated in vacuo. The obtained crude 4-chloro-N-{[3-(4-chlorophenyl)-4-phenyl-4,5-dihydro-1H-pyrazol-1-yl]-[7-(4-fluorophenyl)-7-oxo-heptylamino] methylene}benzenesulfonamide (203 mg) was not further purified. Some characteristic aromatic $^1$H-NMR signals are: (400 MHz, $CDCl_3$) δ 7.12 (d, J~8, 2H), 7.22-7.33 (m, 5H) 7.39 (d, J~8, 2H), 7.50 (d, J~8, 2H), 7.72 (d, J~8, 2H), 7.84 (d, J~8, 2H), 8.05 (d, J~8, 2H).

Part C: 4-Chloro-N-{[3-(4-chlorophenyl)-4-phenyl-4,5-dihydro-1H-pyrazol-1-yl]-[7-(4-fluoro-phenyl)-7-oxo-heptylamino] methylene}benzenesulfonamide (0.203 g, 0.278 mmol) was dissolved in absolute ethanol (10 ml), and O-(2-aminoethyl)hydroxylamine dihydrochloride (61 mg, 1.5 mol equivalent) and pyridine (0.04 ml) were successively added. The resulting mixture was stirred at reflux temperature for 20 hours. The mixture was allowed to attain room temperature. After removal of the solvent in vacuo, the residue was dissolved in dichloromethane and washed successively with an aqueous $KHSO_4$ solution and brine. The organic layer was subsequently dried over $Na_2SO_4$, filtered and concentrated in vacuo to give N-{1-[7-(2-amino-ethoxyimino)-7-[4-(trifluoromethyl)phenyl]heptylamino]-1-[3-(4-chlorophenyl)-4-phenyl-4,5-dihydro-1H-pyrazol-1-yl]-methylidene}-4-chloro-benzenesulfonamide (Compound 1) (0.231 g) as a mixture of E/Z stereoisomers. Melting point: 53-58° C. $^1$H-NMR (400 MHz, $CDCl_3$) δ 1.30-1.67 (m, 8H), 2.80 (t, J=7, 2H), 3.33-3.40 (m, 2H), 3.56-3.66 (m 2H), 4.03 (dd, J=11 and 5, 1H), 4.43-4.55 (m, 3H), 4.60-4.70 (m, 2H), 7.10 (d, J~8, 2H), 7.20-7.37 (m, 7H) 7.48 (d, J~8, 2H), 7.58 (d, J~8, 2H), 7.71 (d, J~8, 2H), 7.82 (d, J~8, 2H), 8.60 (br s, 2H).

2-(2-Chlorophenyl)-1-(4-chlorophenyl)-5-ethyl-1H-imidazole-4-carboxylic acid [7-(2-amino-ethoxyimino)-7-[4-(trifluoromethyl)phenyl] heptyl]amide (Compound 2)

Compound 2

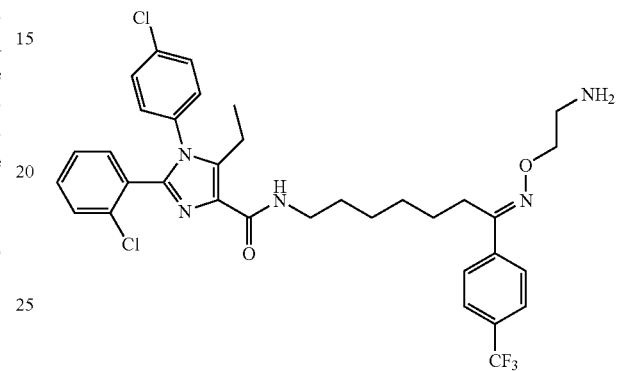

Part A: Ethyl 2-(2-chlorophenyl)-1-(4-chlorophenyl)-5-ethyl-1H-imidazole-4-carboxylate was obtained according to WO03040107. To a magnetically stirred solution of ethyl 2-(2-chlorophenyl)-1-(4-chlorophenyl)-5-ethyl-1H-imidazole-4-carboxylate (5.80 g, 0.0149 mol) in tetrahydrofuran (40 ml) was added a solution of LiOH (0.715 g) in water (40 ml). The resulting mixture was heated at 70° C. for 16 hours. The resulting mixture was allowed to attain room temperature and subsequently treated with concentrated hydrochloric acid (3.5 ml). The tetrahydrofuran was evaporated in vacuo and the resulting mixture was stirred overnight. The formed precipitate was collected by filtration and washed with petroleum ether (40-60) to give 2-(2-chlorophenyl)-1-(4-chlorophenyl)-5-ethyl-1H-imidazole-4-carboxylic acid (4.52 g, 84% yield). $^1$H-NMR (400 MHz, $CDCl_3$): δ 1.09 (t, J=7, 3H), 2.90 (q, J=7, 2H), 3.70 (br s, 1H), 7.12 (dtm J=8 and 2, 2H), 7.22-7.28 (m, 1H), 7.29-7.38 (m, 5H).

Part B: 2-(2-Chlorophenyl)-1-(4-chlorophenyl)-5-ethyl-1H-imidazole-4-carboxylic acid (1.48 g, 4.123 mmol), 7-amino-1-(4-(trifluoromethyl)phenyl)heptan-1-one (1.127 g, 4.123 mmol) [7-amino-1-(4-(trifluoromethyl)phenyl)heptan-1-one was obtained in 62% yield from intermediate E (toluene-4-sulfonic acid 7-oxo-7-[4-(trifluoromethyl)phenyl]heptyl ester) using 7M $NH_3$ in methanol; 72 hours at room temperature, analogously to the synthesis of intermediate G (see also Teubner, 1993)], EDCl, HOAt (0.67 g, 4.95 mmol) and DIPEA (1.44 ml, 8.246 mmol) were successively dissolved in dichloromethane (30 ml) and magnetically stirred at room temperature for 70 hours. The reaction mixture was washed successively with water, 5% aqueous $NaHCO_3$ solution and water and was subsequently dried over $Na_2SO_4$, filtered and concentrated in vacuo to give crude 2-(2-chlorophenyl)-1-(4-chlorophenyl)-5-ethyl-1H-imidazole-4-carboxylic acid {7-[4-(trifluoromethyl)phenyl]-7-oxo-heptyl}amide which was purified by column chromatography (alumina; heptane/ethylacetate=4/1 (v/v)), followed by another column chromatography (silica gel; heptane/ethylacetate=4/1 (v/v)) to give pure 2-(2-chlorophenyl)-1-(4-chlorophenyl)-5-ethyl-1H-imidazole-4-carboxylic acid {7-[4-(trifluoromethyl)-phenyl]-7-oxo-heptyl}amide (1.28 g, 50% yield). $^1$H-NMR (300 MHz, DMSO-d$_6$): δ 0.92 (t, J=7 3H), 1.28-1.68 (m, 8H), 2.84 (q, J=7, 2H), 3.08 (t, J=7, 2H), 3.23 (q, J=7, 2H), 7.30-7.42 (m, 5H), 7.49 (br d, J=8, 2H), 7.56 (d, J=8, 2H), 7.89 (d, J=8, 2H), 8.04 (t, J=6, 1H), 8.15 (d, J=8, 2H).

Part C: 2-(2-chlorophenyl)-1-(4-chlorophenyl)-5-ethyl-1H-imidazole-4-carboxylic acid {7-[4-(trifluoromethyl)phenyl]-7-oxo-heptyl}amide (1.15 g, 1.86 mmol) was dissolved in absolute ethanol (10 ml), and O-(2-aminoethyl)hydroxylamine dihydrochloride (0.276 mg, 1.865 mol) and pyridine (0.18 ml) were successively added. The resulting mixture was stirred at reflux temperature for 20 hours. The mixture was allowed to attain room temperature. After removal of the solvent in vacuo, the residue was dissolved in dichloromethane and washed successively with an aqueous KHSO$_4$ solution and brine. The organic layer was subsequently dried over Na$_2$SO$_4$, filtered and concentrated in vacuo to give 2-(2-chlorophenyl)-1-(4-chlorophenyl)-5-ethyl-1 H-imidazole-4-carboxylic acid [7-(2-amino-ethoxyimino)-7-[4-(trifluoromethyl)phenyl] heptyl]-amide (Compound 2) (1.34 g) as a mixture of E/Z stereoisomers. Melting point: 90-95° C. $^1$H-NMR (400 MHz, CDCl$_3$) δ 1.05 (t, J=7, 3H), 1.34-1.62 (m, 8H), 2.81 (br t, J=7, 2H), 2.93 (q, J=7, 2H), 3.32-3.42 (m, 4H), 4.44-4.50 (m, 2H), 7.11 (d, J=8, 2H), 7.21-7.34 (m, 5H), 7.37 (d, J=8, 1H), 7.49 (br s, 1H), 7.59 (d, J=8, 2H), 7.71 (d, J=8, 2H), 8.65 (br s, 2H).

[2-(2-Chlorophenyl)-1-(4-chlorophenyl)-5-ethyl-1H-imidazole-4-yl] {4-[4-(5-flouro-1H-indol-3-yl)butyl]piperazin-1-yl}methanone (Compound 3)

Compound 3

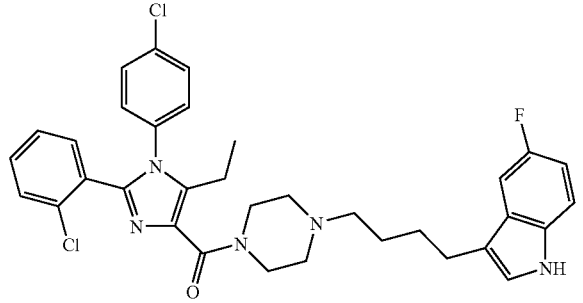

2-(2-Chlorophenyl)-1-(4-chlorophenyl)-5-ethyl-1H-imidazole-4-carboxylic acid (0.880 g, 2.44 mmol) was reacted with intermediate C (5-fluoro-3-[4-(piperazin-1-yl)butyl]-1H-indole), EDCl, HOAt and K$_2$CO$_3$ (1.55 mol equivalent) in dichloromethane (30 ml) at room temperature for 70 hours analogously to the procedure described to prepare Compound 2, Part B to give [2-(2-chlorophenyl)-1-(4-chlorophenyl)-5-ethyl-1H-imidazole-4-yl] {4-[4-(5-flouro-1H-indol-3-yl)butyl]-piperazin-1-yl}methanone (Compound 3) (704 mg, 76% yield) (1.28 gram, 50% yield). Melting point: 91-92° C. $^1$H-NMR (400 MHz, CDCl$_3$) δ 1.03 (t, J=7, 3H), 1.57-1.76 (m, 4H), 2.42 (t, J=7, 2H), 2.48-2.58 (m, 4H), 2.72 (t, J=7, 2H), 2.77 (q, J=7, 2H), 3.81 (br s, 2H), 4.08 (br s, 2H), 6.91 (dt, J~8 and 2, 1 H), 7.01 (d, J =2, 1H), 7.10 (d, J=8, 2H), 7.15-7.35 (m, 8H), 8.08 (br s, 1H).

4-Chloro-N-{[1-[3-(4-chlorophenyl)-4-phenyl-4,5-dihydro-1H-pyrazol-1-yl]-1-{4-[4-(5-fluoro-1H-indol-3-yl)butyl]piperazin-1 -yl}methylidene]-benzenesulfon-amide (Compound 4)

Compound 4

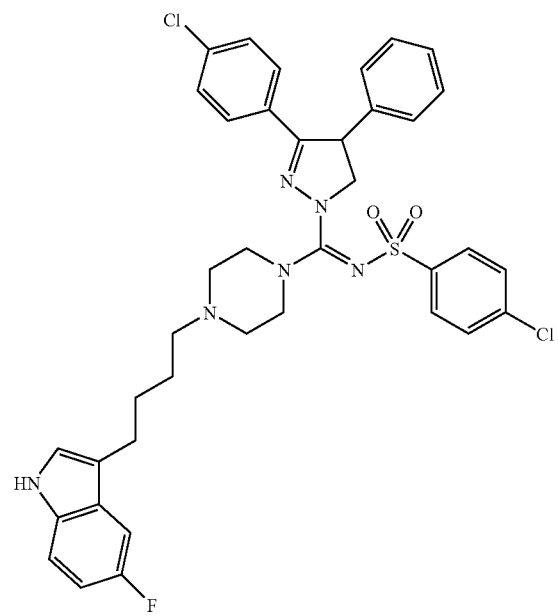

3-(4-Chlorophenyl)-N-[(4-chlorophenyl)sulfonyl]-4-phenyl-4,5-dihydro-1H-pyrazole-1-carboxamide (0.950 g, 2.00 mmol) was dissolved in anhydrous dichloromethane and reacted with DMAP and POCl$_3$, followed by a reaction with intermediate C (5-fluoro-3-[4-(piperazin-1-yl)butyl]-1H-indole) and DIPEA analogously to the procedure to prepare compound 1, Part A to give 4-chloro-N-{[1-[3-(4-chlorophenyl)-4-phenyl-4,5-dihydro-1H-pyrazol-1yl]-1-{4-[4-(5-fluoro-1H-indol-3-yl)butyl]piperazin-1-yl}methylidene]-benzenesulfonamide, (Compound 4) (660 mg, 45% yield). Melting point: 98-102° C. $^1$H-NMR (400 MHz, CDCl$_3$) δ 1.56-1.66 (m, 2H), 1.70-1.80 (m, 2H), 2.47 (t, J=7, 2H), 2.57-2.70 (m, 4H), 2.75 (t, J=7, 2H, 3.69-3.86 (m, 5H), 4.42 (t, J=11, 1H), 4.54 (dd, J=11 and 5, 1H), 6.93 (dt, J~8 and 2, 1H), 7.03 (d, J~2, 1H), 7.10 (d, J=8, 2H), 7.21-7.38 (m, 8H), 7.48 (d, J =8, 2H), 7.83 (d, J=8, 2H), 7.98 (br s, 1H).

Example 5

Formulations Used in Animal Studies

For oral (p.o.) administration: to the desired quantity (0.5-5 mg) of the solid Compound 1 in a glass tube, some glass beads were added and the solid was milled by vortexing for 2 minutes. After addition of 1 ml of a solution of 1% methylcellulose in water and 2% (v/v) of Poloxamer 188 (Lutrol F68), the compound was suspended by vortexing for 10 minutes. The pH was adjusted to 7 with a few drops of aqueous NaOH (0.1 N). Remaining particles in the suspension were further suspended by using an ultrasonic bath.

For intraperitoneal (i.p.) administration: to the desired quantity (0.5-15 mg) of the solid Compound 1 in a glass tube, some glass beads were added and the solid was milled by vortexing for 2 minutes. After addition of 1 ml of a solution of 1% methylcellulose and 5% mannitol in water, the compound was suspended by vortexing for 10 minutes. Finally the pH was adjusted to 7.

Example 6

Pharmacological Methods

In vitro affinity for human cannabinoid $CB_1$ receptors

The affinity of the compounds of the invention for cannabinoid $CB_1$ receptors can be determined using membrane preparations of CHO cells in which the human cannabinoid $CB_1$ receptor is stably transfected in conjunction with [$^3$H] CP-55,940 as radioligand. After incubation of a freshly prepared cell membrane preparation with the [$^3$H]-ligand, with or without addition of compounds of the invention, separation of bound and free ligand is performed by filtration over glass-fiber filters. Radioactivity on the filter is measured by liquid scintillation counting.

In vitro affinity for serotonin reuptake sites

Affinity of the compounds for serotonin reuptake sites was determined using the receptor binding assay described (Habert, 1985).

Example 7

Pharmacological Test Results

Cannabinoid $CB_1$ receptor affinity data and serotonin reuptake inhibition data obtained according to the protocols given above are shown in the table below.

| | In vitro pharmacology | |
|---|---|---|
| | $CB_1$ receptor binding [$^3$H]-CP-55,940 | 5-HT$_{reuptake}$ binding [$^3$H]-paroxetine |
| | $pK_i$ | $pK_i$ |
| Present invention | | |
| Compound 1 | 6.6 | 7.8 |
| Compound 2 | 7.4 | 6.7 |
| Compound 3 | 7.5 | 7.7 |
| Compound 4 | 6.6 | 7.6 |
| $CB_1$ antagonists | | |
| rimonabant | 7.2 | 5.3 |
| SLV319 | 8.1 | <5.0 |
| WO 03/027076 | 7.9 | <4.5 |
| 5-HT reuptake inhibitors | | |
| amitriptyline | <5.0 | 7.2 |
| citalopram | <5.0 | 8.1 |
| fluoxetine | <6.0 | 7.9 |
| fluvoxamine | <5.0 | 8.4 |
| compound A (see below) | <6.0 | 8.9 |
| imipramine | <6.0 | 8.7 |
| indalpine | <6.0 | 8.6 |
| nortriptyline | <5.0 | 7.9 |
| paroxetine | <6.0 | 9.7 |
| sertraline | <5.0 | 8.8 |
| trazodone | <5.0 | 6.7 |
| zimeldine | <5.0 | 7.8 |

| | In vitro pharmacology | |
|---|---|---|
| | $CB_1$ receptor binding [$^3$H]-CP-55,940 | 5-HT$_{reuptake}$ binding [$^3$H]-paroxetine |
| | $pK_i$ | $pK_i$ |

WO 03/027076 compound A

The data given above indicate that the compounds of the invention have a high affinity for both $CB_1$ receptors and 5-HT reuptake sites. Their affinity for $CB_1$ receptors is as high as that of rimonabant, whilst e.g. Compound 1 simultaneously is as potent a serotonin reuptake inhibitor as fluoxetine. This in sharp contrast with for instance a structurally closely related potent $CB_1$ antagonist disclosed in WO 03/027076 (see structure above) which is completely inactive as serotonin reuptake inhibitor. Other $CB_1$ antagonists tested are devoid of affinity for 5-HT reuptake sites, and the 5-HT reuptake inhibitors tested do not have affinity for $CB_1$ receptors.

Example 8

Pharmaceutical Preparations

For clinical use, compounds of formula (1) can be formulated into pharmaceutical compositions that are important and novel embodiments of the invention because they contain the compounds, and, in at least one embodiment, specific compounds disclosed herein. Types of pharmaceutical compositions that may be used include, but are not limited to, tablets, chewable tablets, capsules (including microcapsules), solutions, parenteral solutions, ointments (creams and gels), suppositories, suspensions, and other types disclosed herein, or are apparent to a person skilled in the art from the specification and general knowledge in the art. The active ingredient for instance, may also be in the form of an inclusion complex in cyclodextrins, their ethers or their esters. The compositions can be used for oral, intravenous, subcutaneous, tracheal, bronchial, intranasal, pulmonary, transdermal, buccal, rectal, parenteral or other ways to administer. The pharmaceutical formulation may contain at least one compound of formula (1) in admixture with at least one pharmaceutically acceptable adjuvant, diluent and/or carrier. The total amount of active ingredients suitably is in the range of and in at least one embodiment, from 1% to 25% (w/w). In some embodiments, the amount of active ingredient is greater than about 95% (w/w) or less than about 0.1% (w/w).

The compounds of the invention can be brought into forms suitable for administration by means of usual processes using auxiliary substances such as liquid or solid, powdered ingredients, such as the pharmaceutically customary liquid or solid fillers and extenders, solvents, emulsifiers, lubricants, flavorings, colorings and/or buffer substances. Frequently used auxiliary substances include magnesium carbonate, titanium dioxide, lactose, saccharose, sorbitol, mannitol and other sugars or sugar alcohols, talc, lactoprotein, gelatin, starch, amylopectin, cellulose and its derivatives, animal and vegetable oils such as fish liver oil, sunflower, groundnut or sesame oil, polyethylene glycol and solvents such as, for example, sterile water and mono- or polyhydric alcohols such as glycerol, as well as with disintegrating agents and lubricating agents such as magnesium stearate, calcium stearate, sodium stearyl fumarate and polyethylene glycol waxes. The mixture may then be processed into granules or pressed into tablets. A tablet can be prepared using the ingredients below:

| Ingredient | Quantity (mg/tablet) |
|---|---|
| COMPOUND No. 1 | 10 |
| Cellulose, microcrystalline | 200 |
| Silicon dioxide, fumed | 10 |
| Stearic acid | 10 |
| Total | 230 |

The components are blended and compressed to form tablets each weighing 230 mg.

The active ingredients may be separately premixed with the other non-active ingredients, before being mixed to form a formulation. The active ingredients may also be mixed with each other, before being mixed with the non-active ingredients to form a formulation.

Soft gelatin capsules may be prepared with capsules containing a mixture of the active ingredients of the invention, vegetable oil, fat, or other suitable vehicle for soft gelatin capsules. Hard gelatin capsules may contain granules of the active ingredients. Hard gelatin capsules may also contain the active ingredients together with solid powdered ingredients such as lactose, saccharose, sorbitol, mannitol, potato starch, corn starch, amylopectin, cellulose derivatives, or gelatin.

Dosage units for rectal administration may be prepared (i) in the form of suppositories that contain the active substance mixed with a neutral fat base; (ii) in the form of a gelatin rectal capsule that contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations may be prepared in the form of syrups, elixirs, concentrated drops or suspensions, e.g. solutions or suspensions containing the active ingredients and the remainder consisting, for example, of sugar or sugar alcohols and a mixture of ethanol, water, glycerol, propylene glycol and polyethylene glycol. If desired, such liquid preparations may contain coloring agents, flavoring agents, preservatives, saccharine and carboxymethyl cellulose or other thickening agents. Liquid preparations may also be prepared in the form of a dry powder, reconstituted with a suitable solvent prior to use. Solutions for parenteral administration may be prepared as a solution of a formulation of the invention in a pharmaceutically acceptable solvent. These solutions may also contain stabilizing ingredients, preservatives and/or buffering ingredients. Solutions for parenteral administration may also be prepared as a dry preparation, reconstituted with a suitable solvent before use.

Also provided according to the invention are formulations and 'kits of parts' comprising one or more containers filled with one or more of the ingredients of a pharmaceutical composition of the invention, for use in medical therapy. Associated with such container(s) can be written materials such as instructions for use, or a notice in the form prescribed by a governmental agency regulating the manufacture, use or sale of pharmaceuticals products, which notice reflects approval by the agency of manufacture, use, or sale for human or veterinary administration. The use of formulations of the invention in the manufacture of medicaments for treating a condition wherein antagonism of $CB_1$ receptors and/or inhibition of serotonin re-uptake is required or desired, and methods of medical treatment or comprising the administration of a therapeutically effective total amount of at least one compound of formula (1), either as such or, in the case of prodrugs, after administration, to a patient suffering from, or susceptible to, a condition wherein antagonism of $CB_1$ receptors and/or inhibition of serotonin re-uptake is required or desired.

By way of example, not of limitation, several pharmaceutical compositions are given, comprising exemplary active compounds for systemic use or topical application. Other compounds of the invention or combinations thereof, may be used in place of (or in addition to) said compounds. The concentration of the active ingredient may be varied over a wide range as discussed herein. The amounts and types of ingredients that may be included are well known in the art.

Bibliography

Akaji, K. et al., Tetrahedron Lett. (1994), 35, 3315-3318

Albericio, F. et al., Tetrahedron Lett (1997), 38, 4853-4856

Berge, S. M.: "Pharmaceutical salts", J. Pharmaceutical Science, 66, 1-19 (1977).

Bickel, M. H.,: "The pharmacology and Biochemistry of N-oxides", Pharmacological Reviews, 21(4), 325-355, 1969.

Bodanszky, M. and A. Bodanszky: The Practice of Peptide Synthesis, Springer-Verlag, New York, 1994; ISBN: 0-387-57505-7

Bundgaard, H. (editor), "Design of Prodrugs", Elsevier, 1985.

Bureau, R. et al., J. Chem. Inf. Comput. Sci. 2002, 42, 429-436

Byrn et al., Pharmaceutical Research, 12(7), 945-954, 1995.

De Petrocellis, L. et al,. Br. J. Pharmacol. 2004, 141, 765-774.

Di Marzo, V. et al., Nature Rev. Drug Discov. 2004, 3, 771-784.

Dutta, A. K. et al., Med. Chem. Res. 1994, 5, 54-62

Dwyer & Meilor,: "Chelating agents and Metal Chelates", Academic Press, chapter 7, 1964.

Dyck, B. et al., Bioorg. Med. Chem. Lett. 2004, 14, 1151-1154

Ettmayer, P. et al., "Lessons learned from marketed and investigational prodrugs", J.Med.Chem., 47, 2393-2404, 2004.

Habert, E. et al.,: "Characterisation of [3H]-paroxetine binding to rat cortical membranes", Eur.J.Pharmacol., 118, 107-114, 1985.

Hertzog, D. L. *Expert Opin. Ther. Patents* 2004, 14, 1435-1452;

Järvinen, T. et al., "Design and Pharmaceutical applications of prodrugs", pages 733-796 in: S. C. Gad: "*Drug Discovery Handbook*", John Wiley & Sons Inc., New Jersey, U.S.A., 2005.

Katoch-Rouse, R. et al., *J. Med. Chem.* 2003, 46, 642-645

King, F. D., (editor), page 215 in: "Medicinal Chemistry: Principles and Practice", 1994.

Lambert, D. M. and Fowler, C. J. *J. Med. Chem.* 2005, 48, 5059-5087

Lan, R. et al., *J. Med. Chem.* 1999, 42, 769-776

Landsman, R. S. et al., *Eur. J. Pharmacol.* 1997, 334, R1-R2

Lange, J. H. M. and Kruse, C. G., C. *Curr. Opin. Drug Discovery Dev.* 2004a, 7, 498-506

Lange, J. H. M. et al., *J. Med. Chem.* 2004b, 47, 627-643

Lange, J. H. M. and Kruse, C. G. *Drug Discov. Today* 2005b, 10, 693-702;

Lange, J. H. M. et al., *J. Med. Chem.* 2005b, 48, 1823-1838

Le Fur, G. and Uzan, A., *Biochem Pharmacol.* 1977, 26, 497-503;

Levin, J. I., E. Turos and S. M. Weinreb, *Synth. Commun.*, 12, 989-993, 1982.

Lichtman, A. H. et al., *Prostaglandins Leukotrienes and Essential Fatty Acids* 2002, 66, 269-285

Malleron, J.-L. et al., *J. Med. Chem.* 1993, 36, 1194-1202

Martin, E. W. (Editor), "Remington: *The Science and Practice of Pharmacy*", Mack Publishing Company, 19th Edition, Easton, Pa., Vol 2., Chapter 83, 1447-1462, 1995.

Montalbetti, C. and V. Falque, Tetrahedron, 61, 10827-10852, 2005

Muccioli, G. G. et al., *Curr. Med. Chem.* 2005, 12, 1361-1394;

Pacher, P. and Kecskemeti, V., *Curr. Med. Chem.* 2004, 11, 925-943

Padgett, L. W. Life Sciences 2005, 77, 1767-1798;

Plummer, C. W. et al., *Bioorg. Med. Chem. Lett.* 2005, 15, 1441-1446

Reggio, P. H., *Curr. Pharm. Des.* 2003, 9, 1607-1633

Seltzman, H. H. et al., *J. Chem. Soc. Chem. Commun.* 1995, 1549-1550

Smith, R. A. and Fathi, Z. *IDrugs* 2005, 8, 53-66;

Stella, J., "Prodrugs as therapeutics", *Expert Opin. Ther. Patents*, 14(3), 277-280, 2004.

Teubner, A. and Gerlach, H. *Liebigs Ann. Chem,* 1993, 161-165

Thakur, G. A. et al., *Mini-Rev. Med. Chem.* 2005, 5, 631-640;

Vandevoorde, S. & Lambert, D. M. i Curr. Pharm. Des. 2005, 11, 2647-68.

What is claimed is:

1. A compound of formula (1):

(1)

or a tautomer, stereoisomer, N-oxide, or a pharmacologically acceptable salt of any of the foregoing, wherein:

A is ($A^2$):

($A^2$)

wherein the wavy bond is the point at which the fragment is attached to moiety N (wherein N represents a non-basic nitrogen atom) in formula (1), $R^1$ and $R^2$ independently are chosen from a hydrogen atom, a trifluoromethyl group, and a halogen atom, $R^4$ is chosen from a hydrogen atom, a halogen atom, methyl, ethyl, trifluoromethyl, hydroxymethyl, fluoromethyl, 2,2,2-trifluoroethyl, propyl, methylsulfanyl, methylsulfinyl, methylsulfonyl, ethylsulfanyl, ethylsulfinyl, ethylsulfonyl, $C_{13}$-dialkyl-aminomethyl, pyrrolidin-1-ylmethyl, piperidin-1-ylmethyl, and morpholin-4-ylmethyl group, and the NRTB sequence of formula (1) is chosen from one of the fragments ($NRTB^1$), ($NRTB^2$), ($NRTB^3$), ($NRTB^5$), ($NRTB^6$), ($NRTB^7$), ($NRTB^8$), ($NRTB^9$), and ($NRTB^{10}$):

($NRTB^1$)

($NRTB^2$)

(NRTB³)

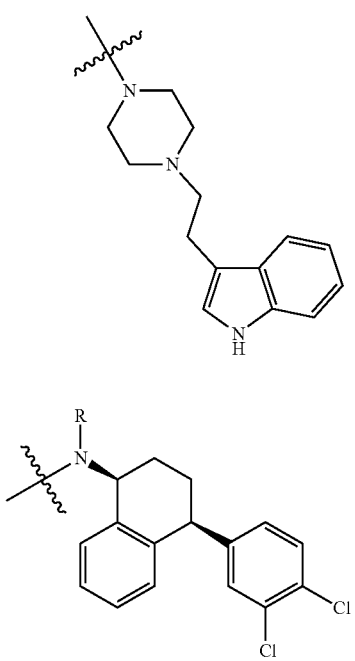

(NRTB⁵)

(NRTB⁶)

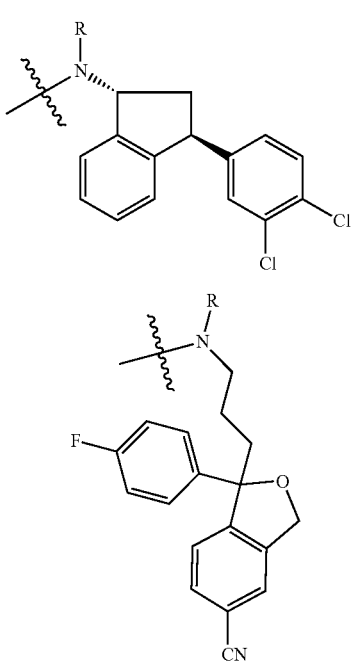

(NRTB⁷)

(NRTB⁸)

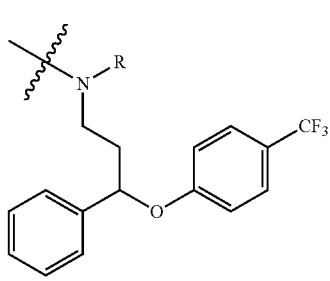

(NRTB⁹)

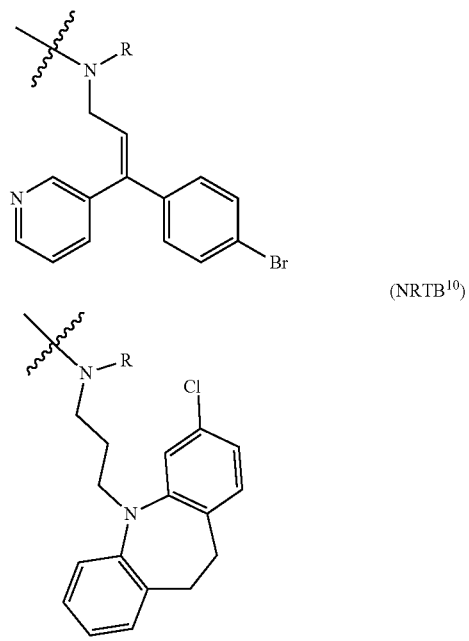

(NRTB¹⁰)

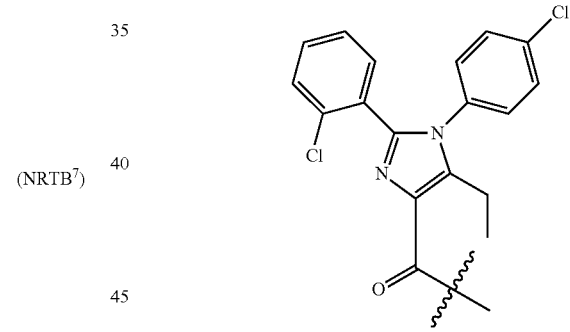

wherein R is chosen from a hydrogen atom and a $(C_1-C_3)$-alkyl group.

2. A compound as claimed in claim 1, wherein A is:

wherein the wavy bond is the point at which the fragment is attached to the non-basic nitrogen atom N in formula (1).

3. A compound chosen from:
2-(2-chlorophenyl)-1-(4-chlorophenyl)-5-ethyl-1H-imidazole-4-carboxylic acid [7-(2-amino-ethoxyimino)-7 [4-(trifluoromethyl)phenyl] heptyl]amide; and

[2-(2-chlorophenyl)-1-(4-chlorophenyl)-5-ethyl-1H-imidazole-4-yl] {4-[4-(5-fluoro-1H-indol3-yl)butyl]piperazin-1-yl}methanone.

4. A compound as claimed in claim 1, wherein said compound is an optically active enantiomer.

5. A pharmaceutical composition comprising, at least one pharmaceutically acceptable carrier and/or at least one pharmaceutically acceptable auxiliary substance, a pharmacologically active amount of at least one compound of formula (1):

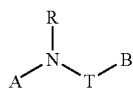
(1)

or a tautomer, stereoisomer, N-oxide, or a pharmacologically acceptable salt of any of the foregoing, wherein:

A is ($A^2$):

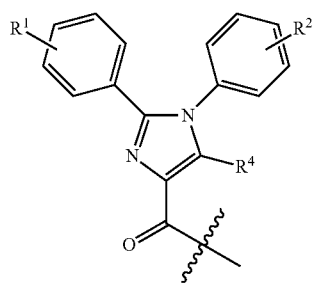
($A^2$)

wherein the wavy bond is the point at which the fragment is attached to moiety N (wherein N represents a non-basic nitrogen atom) in formula (1), $R^1$ and $R^2$ independently are chosen from a hydrogen atom, a trifluoromethyl group, and a halogen atom, $R^4$ is chosen from a hydrogen atom, a halogen atom, methyl, ethyl, trifluoromethyl, hydroxymethyl, fluoromethyl, 2,2,2-trifluoroethyl, propyl, methylsulfanyl, methylsulfinyl, methylsulfonyl, ethylsulfanyl, ethylsulfinyl, ethylsulfonyl, $C_{1-3}$-dialkyl-aminomethyl, pyrrolidin-1-ylmethyl, piperidin-1-ylmethyl, and morpholin-4-ylmethyl group, and the NRTB sequence of formula (1) is chosen from one of the fragments ($NRTB^1$), ($NRTB^2$), ($NRTB^3$), ($NRTB^5$), ($NRTB^6$), ($NRTB^7$), ($NRTB^8$), ($NRTB^9$), and ($NRTB^{10}$):

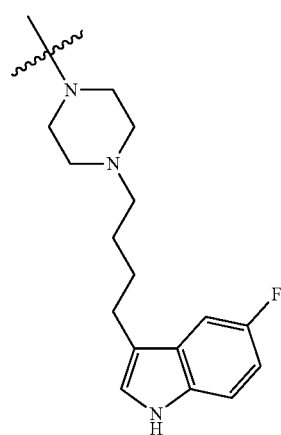
($NRTB^1$)

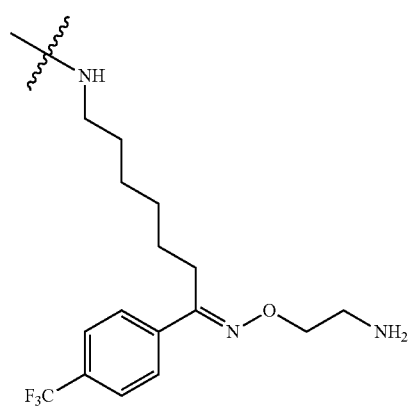
($NRTB^2$)

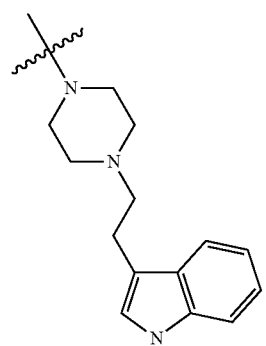
($NRTB^3$)

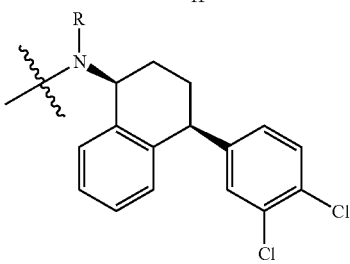
($NRTB^5$)

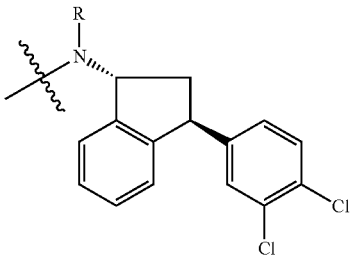
($NRTB^6$)

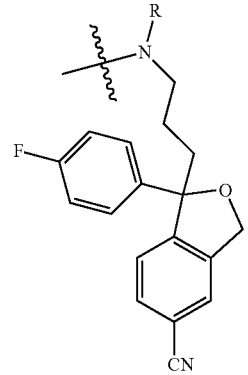
($NRTB^7$)

(NRTB⁸)
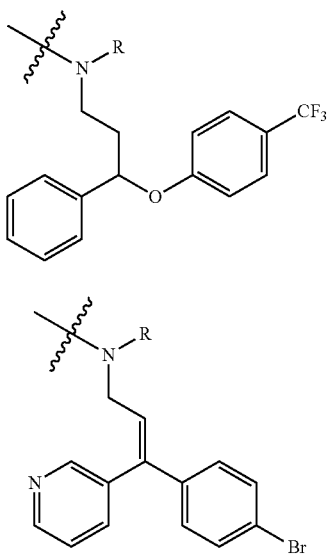
(NRTB⁹)
(NRTB¹⁰)
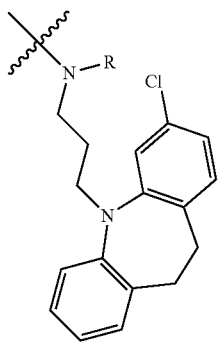
wherein R is chosen from a hydrogen atom and a $(C_1-C_3)$-alkyl group.
* * * * *

UNITED STATES PATENT AND TRADEMARK OFFICE
CERTIFICATE OF CORRECTION

| | | |
|---|---|---|
| PATENT NO. | : 8,138,174 B2 | Page 1 of 1 |
| APPLICATION NO. | : 11/970229 | |
| DATED | : March 20, 2012 | |
| INVENTOR(S) | : Josephus H. M. Lange et al. | |

It is certified that error appears in the above-identified patent and that said Letters Patent is hereby corrected as shown below:

Claim 1, col. 44, line 26, "$C_{13}$" should read -- $C_{1-3}$ --.

Claim 3, col. 46, line 58, "{4-[4-(5-fluoro-1H-indol3-yl)" should read -- {4-[4-(5-fluoro-1H-indol-3-yl) --.

Signed and Sealed this
Twenty-sixth Day of June, 2012

David J. Kappos
*Director of the United States Patent and Trademark Office*